US011382895B2

(12) United States Patent
Day et al.

(10) Patent No.: US 11,382,895 B2
(45) Date of Patent: Jul. 12, 2022

(54) METHODS FOR TREATING INJURY ASSOCIATED WITH EXPOSURE TO AN ALKYLATING SPECIES

(75) Inventors: Brian J. Day, Denver, CO (US); Carl W. White, Denver, CO (US)

(73) Assignee: National Jewish Health, Denver, CO (US)

( * ) Notice: Subject to any disclaimer, the term of this patent is extended or adjusted under 35 U.S.C. 154(b) by 100 days.

(21) Appl. No.: 12/993,469

(22) PCT Filed: May 26, 2009

(86) PCT No.: PCT/US2009/045198
§ 371 (c)(1),
(2), (4) Date: Feb. 11, 2011

(87) PCT Pub. No.: WO2010/016965
PCT Pub. Date: Feb. 11, 2010

(65) Prior Publication Data
US 2011/0136775 A1  Jun. 9, 2011

Related U.S. Application Data

(60) Provisional application No. 61/055,919, filed on May 23, 2008.

(51) Int. Cl.
| A61K 45/06 | (2006.01) |
| A61P 39/06 | (2006.01) |
| A61K 31/555 | (2006.01) |
| A61K 31/4178 | (2006.01) |
| A61K 31/427 | (2006.01) |
| A61K 31/409 | (2006.01) |

(52) U.S. Cl.
CPC ........ *A61K 31/4178* (2013.01); *A61K 31/409* (2013.01); *A61K 31/427* (2013.01); *A61K 31/555* (2013.01); *A61K 45/06* (2013.01)

(58) Field of Classification Search
CPC .... A61K 31/409; A61K 45/06; A61K 31/555; A61P 39/04; A61P 39/06
See application file for complete search history.

(56) References Cited

U.S. PATENT DOCUMENTS

| 2,951,799 | A | 9/1960 | Sharp |
| 4,614,723 | A | 9/1986 | Schmidt |
| 4,657,902 | A | 4/1987 | Kappas et al. |
| 4,746,735 | A | 5/1988 | Kruper, Jr. et al. |
| 4,758,422 | A | 7/1988 | Quay |
| 4,829,984 | A | 5/1989 | Gordon |
| 4,837,221 | A | 6/1989 | Bonnett |
| 4,851,403 | A | 7/1989 | Picker et al. |
| 4,861,760 | A | 8/1989 | Mazuel et al. |
| 4,866,054 | A | 9/1989 | Dori et al. |
| 4,885,114 | A | 12/1989 | Gordon et al. |
| 4,892,941 | A | 1/1990 | Dolphin et al. |
| 4,895,719 | A | 1/1990 | Radhakrishnam |
| 4,911,920 | A | 3/1990 | Jani et al. |
| 4,963,367 | A | 10/1990 | Ecanow |
| 5,010,073 | A | 4/1991 | Kappas et al. |
| 5,051,337 | A | 9/1991 | Sakoda et al. |
| 5,087,438 | A | 2/1992 | Gordon |
| 5,109,016 | A | 4/1992 | Dixon et al. |
| 5,130,245 | A | 7/1992 | Marklund et al. |
| 5,162,519 | A | 11/1992 | Bonnett |
| 5,169,630 | A | 12/1992 | Okaya et al. |
| 5,171,680 | A | 12/1992 | Mullenbach et al. |
| 5,192,757 | A | 3/1993 | Johnson et al. |
| 5,192,788 | A | 3/1993 | Dixon et al. |
| 5,202,317 | A | 4/1993 | Bruice |
| 5,212,162 | A | 5/1993 | Missel et al. |
| 5,217,966 | A | 6/1993 | Bruice |
| 5,223,538 | A | 6/1993 | Fridovich |
| 5,227,405 | A | 7/1993 | Fridovich |
| 5,236,914 | A | 8/1993 | Meunier |
| 5,236,915 | A | 8/1993 | Fiel |
| 5,248,603 | A | 9/1993 | Marklund et al. |
| 5,262,532 | A | 11/1993 | Tweedie et al. |
| 5,277,908 | A | 1/1994 | Beckman et al. |
| 5,281,616 | A | 1/1994 | Dixon et al. |
| 5,284,647 | A | 2/1994 | Niedballa et al. |
| 5,366,729 | A | 11/1994 | Marklund et al. |
| 5,403,834 | A | 4/1995 | Malfroy-Camine et al. |
| 5,403,841 | A | 4/1995 | Lang et al. |
| 5,405,369 | A | 4/1995 | Selman et al. |
| 5,472,691 | A | 12/1995 | Marklund et al. |
| 5,493,017 | A | 2/1996 | Thieren et al. |

(Continued)

FOREIGN PATENT DOCUMENTS

| CA | 02493199 A | 1/2005 |
| EP | 127797 A1 | 12/1984 |

(Continued)

OTHER PUBLICATIONS

Smith K.R. et al. Inhibition of Tobacco Smoke-Induced Lung Inflammation by a Catalytic Antioxidant. Free Radical Biology & Medicine, vol. 33, No. 8, pp. 1106-1114 (2002).*
Smith C.J. et al. Utility of the mouse dermal promotion assay in comparing the tumorigenic potential of cigarette mainstream smoke. Food and Chemical Toxicology 44, 1699-1706 (2006).*
Rodgman A. and Perfetti T.A. eds. The Chemical Components of Tobacco and Tobacco Smoke. CRC Press 2009; Ch. 19, pp. 893-906.*

(Continued)

*Primary Examiner* — Jeffrey S Lundgren
*Assistant Examiner* — Chris E Simmons
(74) *Attorney, Agent, or Firm* — Sheridan Ross P.C.

(57) ABSTRACT

Compounds may be administered to prevent or rescue organ injury following exposure to alkylating agents, such as sulfur mustards. The compounds may be substituted metalloporphyrins.

5 Claims, 15 Drawing Sheets

(56) References Cited

U.S. PATENT DOCUMENTS

| | | | |
|---|---|---|---|
| 5,563,132 A | 10/1996 | Bodaness | |
| 5,599,924 A | 2/1997 | Therien et al. | |
| 5,604,199 A | 2/1997 | Funanage | |
| 5,610,293 A | 3/1997 | Riley et al. | |
| 5,637,578 A | 6/1997 | Riley et al. | |
| 5,674,467 A | 10/1997 | Maier et al. | |
| 5,747,026 A | 5/1998 | Crapo | |
| 5,767,272 A | 6/1998 | Wijesekera et al. | |
| 5,834,509 A | 11/1998 | Malfroy-Camine et al. | |
| 5,874,421 A | 2/1999 | Riley et al. | |
| 5,948,771 A | 9/1999 | Danziger | |
| 5,976,498 A | 11/1999 | Neumann et al. | |
| 5,976,551 A | 11/1999 | Mottez et al. | |
| 5,994,339 A | 11/1999 | Crapo et al. | |
| 5,994,410 A | 11/1999 | Chiang et al. | |
| 6,013,241 A | 1/2000 | Marchal et al. | |
| 6,046,188 A | 4/2000 | Malfroy-Camine et al. | |
| 6,060,467 A | 5/2000 | Buelow et al. | |
| 6,084,093 A | 7/2000 | Riley et al. | |
| 6,087,493 A | 7/2000 | Wheelhouse et al. | |
| 6,103,714 A | 8/2000 | Fridovich et al. | |
| 6,127,356 A | 10/2000 | Crapo et al. | |
| 6,180,620 B1 | 1/2001 | Salvemini | |
| 6,204,259 B1 | 3/2001 | Riley et al. | |
| 6,214,817 B1 | 4/2001 | Riley et al. | |
| 6,245,758 B1 | 6/2001 | Stern et al. | |
| 6,372,727 B1 | 4/2002 | Crow et al. | |
| 6,395,725 B1 | 5/2002 | Salvemini | |
| 6,403,788 B1 | 6/2002 | Meunier et al. | |
| 6,417,182 B1 | 7/2002 | Abrams et al. | |
| 6,479,477 B1 | 11/2002 | Crapo et al. | |
| 6,544,975 B1 | 4/2003 | Crapo et al. | |
| 6,548,045 B2 | 4/2003 | Sakata et al. | |
| 6,566,517 B2 | 5/2003 | Miura et al. | |
| 6,573,258 B2 | 6/2003 | Bommer et al. | |
| 6,583,132 B1 | 6/2003 | Crapo et al. | |
| 6,602,998 B2 | 8/2003 | Kobuke et al. | |
| 6,624,187 B1 | 9/2003 | Pandey et al. | |
| 6,916,799 B2 | 7/2005 | Fridovich et al. | |
| 7,189,707 B2 * | 3/2007 | Crapo | A61K 31/409 514/185 |
| 7,470,677 B2 | 12/2008 | Crapo et al. | |
| 8,217,026 B2 * | 7/2012 | Crapo | A61K 31/409 514/185 |
| 2002/0042407 A1 | 4/2002 | Fridovich et al. | |
| 2002/0058643 A1 | 5/2002 | Cherian et al. | |
| 2003/0050297 A1 * | 3/2003 | Crapo | A61K 31/409 514/185 |
| 2004/0023941 A1 | 2/2004 | Crapo et al. | |
| 2005/0186261 A1 * | 8/2005 | Avelar | A61K 31/335 424/445 |
| 2007/0066541 A1 * | 3/2007 | Hughes | A61K 31/498 514/559 |
| 2007/0149498 A1 | 6/2007 | Crapo et al. | |
| 2007/0197496 A1 | 8/2007 | Crapo et al. | |
| 2008/0139524 A1 * | 6/2008 | Bailey | C07D 487/22 514/185 |

FOREIGN PATENT DOCUMENTS

| | | |
|---|---|---|
| EP | 186962 A1 | 7/1986 |
| EP | 282899 A2 | 9/1988 |
| EP | 0 284 645 A2 | 10/1988 |
| EP | 336879 A1 | 10/1989 |
| EP | 337601 A1 | 10/1989 |
| EP | 345171 A1 | 12/1989 |
| EP | 414915 A1 | 3/1991 |
| EP | 462836 A2 | 12/1991 |
| EP | 524161 A1 | 1/1993 |
| EP | 532327 A2 | 3/1993 |
| EP | 1616869 A1 | 1/2006 |
| FR | 2676738 A1 | 11/1992 |
| JP | 02-289844 | 11/1990 |
| JP | 3273082 | 12/1991 |
| RU | 1287521 A1 | 10/1996 |
| WO | WO 91/04315 A1 | 4/1991 |
| WO | WO 91/19977 A1 | 12/1991 |
| WO | WO 92/07935 A1 | 5/1992 |
| WO | WO 92/08482 A1 | 5/1992 |
| WO | WO 92/15099 A1 | 9/1992 |
| WO | WO 93/02090 A1 | 2/1993 |
| WO | WO 94/04614 | 3/1994 |
| WO | WO 94/05285 A1 | 3/1994 |
| WO | WO 94/24116 | 10/1994 |
| WO | WO 95/10185 A1 | 4/1995 |
| WO | 1995/017876 | 7/1995 |
| WO | WO 95/31197 A1 | 11/1995 |
| WO | WO 96/09038 A2 | 3/1996 |
| WO | WO 96/09053 A1 | 3/1996 |
| WO | WO 96/40148 A1 | 12/1996 |
| WO | WO 96/40223 A1 | 12/1996 |
| WO | WO 97/06824 A2 | 2/1997 |
| WO | WO 97/06830 A1 | 2/1997 |
| WO | WO 97/06831 A1 | 2/1997 |
| WO | WO 97/33588 A1 | 9/1997 |
| WO | WO 97/33877 A1 | 9/1997 |
| WO | WO 98/33503 A1 | 8/1998 |
| WO | WO 98/58636 A1 | 12/1998 |
| WO | WO 99/07687 | 2/1999 |
| WO | WO 99/10317 | 3/1999 |
| WO | WO 99/23097 A1 | 5/1999 |
| WO | WO 99/55388 A1 | 11/1999 |
| WO | WO 00/04868 A2 | 2/2000 |
| WO | WO 00/19993 A2 | 4/2000 |
| WO | WO 00/23568 A2 | 4/2000 |
| WO | WO 00/43395 A1 | 7/2000 |
| WO | WO 00/72893 A2 | 12/2000 |
| WO | WO 00/75144 A2 | 12/2000 |
| WO | WO 01/26655 A1 | 4/2001 |
| WO | 02/078670 A1 | 10/2001 |
| WO | WO 01/96345 A1 | 12/2001 |
| WO | WO 02/004454 A1 | 1/2002 |
| WO | 02/060383 A2 | 8/2002 |
| WO | 2002/0060383 A2 | 8/2002 |
| WO | WO 02/096366 A2 | 12/2002 |
| WO | 2005/077269 A1 | 8/2005 |
| WO | WO 2006/083381 * | 8/2006 |
| WO | 2006/116353 | 11/2006 |
| WO | 11/028935 A2 | 3/2011 |

OTHER PUBLICATIONS

Shohrati et al. Therapeutic effect of N-acetyl cysteine on mustard gas exposed patients: evaluating clinical aspect in patients with impaired pulmonary function test. Resp. Med. 102, 443-448 (2008) (available online Nov. 26, 2007).*

Gautam et al. Comparative toxicity studies of sulfur mustard (2,2'-dichloro diethyl sulfide) and monofunctional sulfur mustard (2-chloroethyl ethyl sulfide), administered through various routes in mice. J. Med. CBR Def vol. 4 (Feb. 28, 2006).*

Aeolus Pharmaceuticals' Lead Compound to Be Tested in NIH Sponsored Mustard Gas Treatment Study. Aeolus Pharmaceuticals Press Release (May 23, 2007).*

Rabbani et al. (Int. J. Radiation Oncology Biol. Phys., vol. 67, No. 2, pp. 573-580, Feb. 1, 2007). (Year: 2007).*

Sciuto et al. ("Therapeutic Treatments of Phosgene-Induced Lung Injury." Inhalation Toxicology, 16:565-580, 2004) (Year: 2004).*

Korkmaz et al. ("Molecular targets against mustard toxicity: implication of cell surface receptors, peroxynitrite production, and PARP activation." Arch Toxicol (2006) 80: 662-670) (Year: 2006).*

Archibald et al., Investigations of the State of the Manganese in Lactobacillus plantarum, Archives of Biochemistry and Biophysics 215(2):589-596 (1982).

Archibald et al., Manganese and Defenses against Oxygen Toxicity in Lactobacillus plantarum, Journal of Bacteriology 145(1):442-451 (1981).

Archibald et al., Manganese, Superoxide Dismutase, Oxygen Tolerance in Some Lactic Acid Bacteria, Journal of Bacteriology 146(3):928-936 (1981).

Archibald et al., The Scavenging of Superoxide Radical by Manganous Complex: In Vitro, Archives of Biochemistry and Biophysics 214(2):452-463 (1982).

(56) References Cited

OTHER PUBLICATIONS

Balch, "Geometric and electronic structure and dioxygen sensitivity of the copper complex of octaethylbilindione, a biliverdin analog", J. Am. CheM. Soc. 115(25):12206-12207 (1993).
Balch, "Isolation and characterization of an iron biliverdin-type complex that is formed along with verdohemochrome during the coupled oxidation of iron (II) octaethylporphyrin", Am. Chem. Soc. 115(20):9056-9061 (1993).
Balch, "Solid-state self-association of the two-electron oxidation product of a biliverdin analogue", J. Chem. Soc. Chem. Commun. 6:643-644 (1995).
Bamford et al., "The Squalestatins: Synthesis and Biological Activity of Some C3-Modified Analogues; Replacement of a Carboxylic Acid or Methyl Ester with an Isoelectric Heterocyclic Functionality", J. Med. Chem. 38:3502-3513 (1995).
Batinic-Haberle et al, "Manganese(iII) meso-tetrakis(ortho-N-alkylpyridyl)porphyrins. Synthesis, characterization, and catalysis of O2.- dismutation", J. Chem. Soc. Dalton Trans., pp. 2689-2696 (2002).
Batinic-Haberle et al, Relationship among Redox Potentials, proton Dissociation Constants of Pyrrolic Nitrogens, and in Vivo and in Vitro Superoxide Dismutating Activities of Manganese(III) and Iron(III) Water-Soluble Porphyrins Inorg. Chem. 38:4011-4022 (1999).
Batinic-Haberle et al, "The Ortho Effect Makes Manganic Meso-Tetrakis-(N-Methylpyridinium-2-YL)(MnTM-2-PyPs+) a Powerful And Useful Superoxide Dismutase Mimic", Oxygen '97, The 4th Annual Meeting of the Oxygen Society, Council Meeting, The Palace Hotel, San Francisco, California, Nov. 20-24, 1997,—p. 38, Abstract 1-8.
Batinic-Haberle et al., "A Potent Superoxide Dismutase Mimic" Manganese[B]-Octabromo-meso-tetrakis (Nmethylpyridinium-4-yl)Porphyrin, Archives of Biochemistry and Biophysics 343(2):225-233 (1997).
Baudry et al., "Salen-Manganese Complexes are Superoxide Dismutase-Mimics", Biochemical and Biophysical Research Communication 192(2):964-968 (1993).
Beckman et al, "Apparent hydroxyl radical production by peroxynitrite: Implications for endothelial injury from nitric oxide and superoxide", Proc. Natl. Acad. Sci. USA 87:1620-1624 (1990).
Bedioui et al., "Metalloporphyrin-Polypyrrole Film Electrode: Characterization and Catalytic Application", J. Electroanal. Chem. 207:87-99 (1986).
Beil et al, "Helicobacter pylori Reduces Intracellular Glutathione in Gastric Epithelial Cells", Digestive Diseases and Sciences 45(9):1769-1773 (2000).
Berezin et al, Effect of ligand structure on the kinetic stability of tetraphenylporphyrin complexes of zinc and cadmium, Zhurnal Neorganicheskoi Khimii 25(10):2645-2652 (1980).
Berezin et l, "Factors determining the stability of complexes of copper with p-substituted derivatives of tetraphenylporphine", Zhurnal Fizicheskoi Khimii 53(11):2716-2719 (1979)—English Abstract.
Beyer, Jr., Characterization of a Superoxide Dismutase Mimic Prepared from Desferrioxamine and Mn02, Archives of Biochemistry and Biophysics 271(1):149-156 (1989).
Bishop et al., "The Reaction of Thiomides with Phosphorus Ylides", J. Org. Chem. 56:5079-5091 (1991).
Bloodsworth et al, "Manganese-Porphyrin Reactions with Lipids and Lipoproteins", Free Radical Biology & Medicine 28(7):1017-1029 (2000).
Bockhorst and Hoehn-Berlage, "An Optimized Synthesis of Manganese meso-Tetra(4-sulfonato phenyl) porphine: A Tumor-Selective MRI Contrast Agent", Tetrahedron 50(29):8657-8660 (1994).
Boissinot et al., "Rational Design and Expression of a Heparin-Targeted Human Superoxide Dismutase", Biochemical and Biophysical Research Communication 190(1):250-256 (1993).
Bors et al., "An expanded function for superoxide dismutase", Chemical Abstracts 115:388 (1991), Abstract No. 109185h.

Bottino, Rita et al., "Preservation of human islet cell functional mass by anti-oxidative action of a novel SOD mimic compound", Diabetes, 51:2561-7, Aug. 2002.
Brigelius et al., "Superoxide Dismutase Activity of Low Molecular Weight Cu2+-Chelates Studiedby Pulse Radiolysis", FEBS Letters 47(1):72-75 (1974).
Burke, "Photochemical and thermal transformations of phytochrome", Chem. Physiol. Bile Pigm., Int. Symp., pp. 509-517 (1975).
Butje et al., "Electronic Spectra, Resonance Raman Spectra and Solution Properties of Water-soluble (Cu(II), Ni(II) and Co(III) Porphyrins", Inorg. Chim. Acta 167:97-108 (1990).
Callot and Schaeffer, "Ring contraction of homoporphyrins to porphyrins, meso-Reactivity of 5,10,15Triphenylporphin and Porphin", J. Chem. Research (S):51 (1978).
Chung et al, "Protective effects of heroin and tetrakis(4-benzoic acid)porphyrin on bacterial mutagenesis and mouse skin carcinogenesis induced by 7,12-dimethylbenz[a]anthracene", Mutation Research 472:139-145 (2000).
Clyde et al., "Distribution of Manganese Superoxide Dismutase mRNA in Normal and Hyperoxic Rat Lung", American Journal of Respiratory Cell and Molecular Biology 8:530-537 (1993).
Collman et al., "Synthesis of "Face to Face" Porphyrin Dimers Linked by 5,15-Substituents: Potential Binuclear Multielectron Redox Catalysts", J. Am. Chem. Soc. 103:516-533 (1981).
Comhair et al., "Rapid loss of superoxide dismutase activity during antigen-induced asthmatic response", Lancet 355 (9204):624 (2000).
Crapo and Tierney "Superoxide dismutase and pulmonary oxygen toxicity", Am. J. Physiol. 226:1401-1407 (1974).
Crapo et al., "Superoxide Dismutase and Oxygen Toxicity", Clinical Research, p. 222, 1991.
Crapo et al., "The Failure of Aerosolized Superoxide Dismutase to Modify Pulmonary Oxygen Toxicity", American Review of Respiratory Disease 115:1027-1033 (1977).
Crapo et al., 721195, Document No. 123:218443 (1994).
Darr et al., "A Mimic of Superoxide Dismutase Activity Based Upon Desferrioxamine B and Manganese(IV)", Archives of Biochemistry and Biophysics 258(2):351-355 (1987).
Datta-Gupta et al., "Synthetic Porphyrins II Preparation and Spectra of Some Metal Chelates of para", Journal of Substituted-mesa-TetraDhenylporphines, J. of Pharmaceutical Science 57(2):300-304 (1968).
Datta-Gupta et al., "Synthetic Porphyrins. I. Synthesis and Spectra of Some para-Substituted mesoTetraphenylporphines (1)", J. Heterocycl. Chem. 3:495-502 (1966).
Davila et al., "Sterically-Hindered Zinc Porphyrins for Solar-Energy Conversion", J. Chem. Soc., Chem. Commun., pp. 525-527 (1987).
Day et al., "A Metalloporphyrin Superoxide Dismutase Mimetic Protects Against Paraquat-Induced Endothelial Cell Injury, in Vitro", The Journal of Pharmacology and Experimental Therapeutics 275(3):1227-1232 (1995).
Day et al., "Manganic Porphyrins Possess Catalase Activity . . . ," Arch. Biochem. Biophys., vol. 347, No. 2, pp. 256-262 (1997).
De Peretti et al., "Imidazol[2,1-b]benzoxazole-3-acetamide derivatives, their preparation, and their therapeutic use", Chemical Abstracts 121:1016, Abstract No. 121:200896u, 1994.
Dealvare et al., "Mechanism of Superoxide Anion Scavenging Reaction by Bis-(Salicylato)-Copper(II) Complex", Biochemical and Biophysical Research Communications 69(3):687-694(1976).
Deune et al., "Prevention of Ischemia-Reperfusion Injury with a Synthetic Metalloprotein Superoxide Dismutase Mimic, SC52608", Plastic and Reconstructive Surgery 98(4):711-718 (1996).
Diguiseppi et al., "Putative Superoxide Dismutase Activity of Iron-EDTA: A Reexamination", Archives of Biochemistry and Biophysics 203(1):145-150 (1980).
Dwyer et al., "Protective Properties of Tin- and Manganese-Centered Porphyrins Against Hydrogen PeroxideMediated Injury in Rat Astroglial Cells", J. Neurochem 71:2497 (1998).
Elangovan and Krishnan, "Photophysical properties of porphyrin amphiphiles bearing pyridinium alkyl groups", Chemical Physics Letters 194(1,2):139-146 (1992), XP000986304.

(56) References Cited

OTHER PUBLICATIONS

El-Far and Pimstone, "Selective in Vivo Tumor Localization of Uroporphyrin Isomer I in Mouse Mammary Carcinoma: Superiority over Other Porphyrins in a Comparative Study", Cancer Research 46:34390-4394 (1986).
Epp et al., "Superoxide Dismutase Activity of Manganese Chelates", 76-78 (1986).
Fajer et al., "Tr-Cation Radicals and Dications of Metalloporphyrins", Journal of the American Chemical Society 92 (11):3451-3459 (1970).
Falk, "Constritions to the chemistry of pyrrolic pigments", Tetrahedron 37(4):761-7 (1981).
Faulkner et al., "Characterization of Mn(III) Complexes of Linear and Cyclic Desferrioxamines as Mimics of Superoxide Dismutase Activity", Archives of Biochemistry and Biophysics 310(2):341-346 (1994).
Faulkner et al., Stable Mn(III) Porphyrins Mimic Superoxide Dismutase in Vitro and Substitute for it in Vivo, The Journal of Biological Chemistry 269(38):23471-23476 (1994).
Folz et al., "Extracellular Superoxide Dismutase (SODS): Tissue-Specific Expression, Genomic Characterization, and Computer-Assisted Sequence Analysis of the Human EC SOD Gene", Genomics 22:162-171 (1994).
Foran et al., "Effect of Electrolyte Concentration on Axial Anion Ligation in Manganese(III) mesa Tetraphenylporphyrin Chlorides", Inorg. Chem. 31:1463-1470 (1992).
Gassman et al., "Electronic Effects of Peripheral Substituents in Porphyrins: X-ray Photoelectron Spectroscopy and ab Initio Self-Consistent Field Calculations", J. Am. Chem. Soc. 114:9990-10000 (1992).
Gauuan et al, "Superoxide dismutase mimetics: synthesis and structure-activity relationship study of MnTBAP analogues", Bioorganic & Medicinal Chemistry 10(9):3013-3021 (2002).
Ghosh, "Substituent Effects on Valence Ionization Potentials of Free Base Porphyrins: Local Density Functional Calculations and Their Relevance to Electrochemical and Photoelectron Spectroscopic Studies", J. Am. Chem. Soc. 117:4691-4699 (1995).
Giraudeau et al., "Substituent Effects in the Electroreduction of Porphyrins and Metalloporphyrins", Journal of the American Chemical Society 101(14):3857-3862 (1979).
Gonzalez et al., "EUK-8, a Synthetic Superoxide Dismutase and Catalase Mimetic, Ameliorates Acute Lung Injury in Endotexemic Swine", The Journal of Pharmacology and Experimental Therapeutics 275(2):798-806 (1995).
Groves and Marla, "Peroxynitrite-Induced DNA Strand Scission Mediated by a Manganese Porphyrin", J. Am. Chem. Soc. 117(37):9578-9579 (1995).
Halliwell, Barry, "The Superoxide Dismutase Activity of Iron Complexes", FEBS Letters 56(1):34-38 (1975).
Hambright et al, "Synthesis and Characterization of New Isomeric Water-Soluble Porphyrins Tetra(2-Nmethylpyridyl)porphine and Tetra(3-N-methylpyridyl)porphine", Inorganic Chemistry 15(9):2314-2315 (1976).
Hambright et al., "An acid solvolysis kinetic study of manganese(II)-tetra(2-N-methylpyridyl)porphine", J. Inorg. Chem. 39:1102-1103 (1977).
Hambright et al., "Manganese(III) porphyrin isomers: polarography and stannous ion reduction kinetics", Porphyrin Chem. Adv., editor: Longo, [Pap. Porphyrin Symp.], pp. 284-292, Meeting Date 1977.
Harriman et al., "Photochemistry of Manganese Porphyrins Part 2.—Photoreduction", pp. 1543-1552, 1998.
Harriman et al., "Photochemistry of Manganese Porphyrins", J. Chem. Soc. 275:1532-1542 (1979).
Hunt et al., "Amphiphilic peroxynitrite decomposition catalysts in liposomal assemblies", Chemistry & Biology 4 (11):845-858 (1997).
Ilan et al., "Superoxide Dismuting Activity of an Iron Porphyrin", Inorg. Nucl. Chem. Letters 17(3/4):93-96 (1981) Couple, J. Phys. Chem. 86:1842-1849 (1982).
Inoue et al., "Expression of a Hybrid Cu/Zn-type Superoxide . . . ," J. Bio. Chem., vol. 266, No. 25, pp. 16409-16414 (1991).

International Search Report from International Application No. PCT/US2000/002062 dated May 19, 2000, 1 page.
International Search Report for International Application No. PCT/JP2000/008558 dated Jan. 4, 2002, 5 pages.
International Search Report for International Application No. PCT/US2002/017144 dated Aug. 22, 2002, 2 pages.
Jin et al., "A new route to water soluble porphyrins: phosphonium and ammonium type cationic porphyrins and self-assembly", Chem. Commun., pp. 1939-1940 (1996).
Joester et al., "Superoxide Dismutase Activity of Cu2+-Amino Acid Chelates", FEBS Letters 25(1):25-28 (1972).
Kariya et al., "Superoxide Dismutase (SOD) Activity with Fe-chlorin e6-Na and Suppression of Malignant Tumor Growth in Rats", Cancer Biotheraphy 10(2):139-145 (1995).
Kaufmann et al., "Separation of the Rotational Isomers of Tetrakis(N-methyl-2-pyridiniumyl)porphyrin and Crystal Structure of a,a,a,R-(Tetrakis(N-methy1-2-pyridiniumyl)porphyrin)copper Hexacyanoferrate", Inorg. Chem. 34:5073-5079 (1995).
Keinan et al., "Catalytic Antibodies. Circular Dichroism and UV-Vis Studies of Antibody-Metalloporphyrin Interactions", Inorg. Chem. 31:5433-5438 (1992).
Kobayashi et al, "Oxidative Stress Relief for Cancer-Bearing Hosts by the Protein-Bound Polysaccharide of Coriolus versicolor QUEL with SOD Mimicking Activity", Cancer Biotherapy 9(1):55-62 (1994).
Koerner "Carbon monoxide production during the oxygenation of cobalt complexes of linear etrapyrroles", Inorg. Chem. 37(5):982-988 (1998).
Konorev et ai, "Cell-Permeable Superoxide Dismutase and Glutathione Peroxidase Mimetics Afford Superior Protection against Doxorubicin-Induced Cardiotoxicity: The Role of Reactive Oxygen and Nitrogen Intermediates", Archives of Biochemistry and Biophysics 368(2):421-428 (1999).
Kumar et al., "Radioprotection by Antioxidant Enzymes and Enzyme Mimetics", Pharmac. Ther. 39:301-309 (1988).
Laehdesmaeki et al, "Detection of Oxygen Consumption of Cultured Adherent Cells by Bead Injection Spectroscopy", Analytical Chemistry 71(22):5248-5252 (1999).
Lappin, "Part III Bioinorganic Studies", Inorganic Reaction Mechanisms 7:334-343 (1981).
Lee and Smith, "Syntheses of symmetrically substituted 5-alkyl- and 5-aryl-dihydrodipyrrins and of porphyrins and bisporphyrins therefrom", J. Chem. Soc. Perkin Trans 1:1215-1227 (1997).
Lee et al., "Rapid decomposition of peroxynitrite by manganese porphyrin-antioxidant redox couples", Bioorganic & Medical Chemistry Letters 7(22):2913-2918 (1997).
Leonidas et al., "5,10,15,20-Tetrakis(, , ,—(N-tert-butyl-carbamoyl)phenyl)porphyrin: Syntheses and Redox Properties of Zinc(II) and Copper(II) Complexes", J. Org. Chem. 54:6135-6138 (1989).
Libby et al., "Cationic Porphyrin Derivatives As Inhibitors of Polyamine Catabolism", Biochemical Pharmacology 50 (9):1527-1530 (1995).
Lindsey et al, "Rothemund and Adler-Longo Reactions Revisited: Synthesis of Tetraphenylphorins under Equilibrium Conditions", J. Org. Chem. 52:827-836 (1987).
Lindsey et al, "Synthesis of tetraphenylporphyrins under very mild conditions", Tetrahedron Letters 27(41):4969-4970 (1986).
Lindsey et al, i262Cf Plasma Desorption Mass Spectrometry in the Synthesis of Porphyrin Model Systems, Anal. Chem. 64(22):2804-2814 (1992).
Liochev et al., A Cationic Manganic Porphyrin Inhibits Uptake of Paraquat by *Escherichia coil*, Archives of Biochemistry and Biophysics 321(1):271-275 (1995).
Longo et al., "The Synthesis and Som e Physical Properties of ms-Tetra(pentafluorophenyl)-porphin and msTetraphenylporphines (1)", Notes 6:927-931 (1969).
Lord, "Redox characteristics of nickel and palladium complexes of the open-chain tetrapyrrole octaethylbilindione: a biliverdin model", Inorg. Chem. 39(6):1128-34 (2000).
Louati et al., "Homophophyrines: Effets D'Une Coupure De Conjugaison Cyclique Sur La Reactivite Redox Des Porphyrines", Nouv. J. Chim. 2:163-168 (1978).

(56) References Cited

OTHER PUBLICATIONS

Lowe et al., "Comparison of the cardiovascular effects of two novel superoxide dismutase mimetics, SC-55858 and SC-54417, in conscious dogs", European Journal of Pharmacoloty 304:81-86 (1996).
Mabley et al, "Part II: Beneficial Effects of the Peroxynitrite Decomposition Catalyst FP15 in Murine Models of Arthritis and Colitis", Molecular Medicine 8(10):581-590 (2002).
Mackensen et al., "Neuroprotection from Delayed Postischemic Administration of a Metalloporphyrin Catalytic Antioxidant", The Journal of Neuroscience 21(13):4582-4592 (2001).
Madakyan et al., "New watersoluble metal complexes of meso-tetrakis[3-N-(2'-hydroxy ethyl)pyridyl]porphyrins and their pharmacological activity", Arm., Khim. Zh. 42(11):724-728—Chemical Abstracts 113:653—Abstract No. 114907h, 1972.
Madakyan et al., "Some metal complexes of meso-tetrakis (3-N-substituted pyridyl) porphyrins and their bioactivity", Arm. Khim. Zh. 42(10):642-646 (1989).
Malinski et al., "Characterization of Conductive Polymeric Nickel(II) Tetrakis(3-methoxy-4-hydroxyphenyl)Porphyrin as an Anodic Material for Electrocatalysis", J. Electrochem. Soc. 138(7):2008-2015 (1991).
Marx, "Role of Gene Defect in Heredity ALS Clarified", Science 261:986 (1993).
McClune et al., "Catalysis of Superoxide Dismutation by Iron-Ethylenediaminetetraacetic Acid Complexes. Mechanism of the Reaction and Evidence for the Direct Formation of an Iron(III)-Ethylenediaminetetraacetic Acid Peroxo Complex from the Reaction of Superoxide with Iron(ll)-Ethylenediaminetetraacetic Acid", Communications to the Editor, p. 5220-2 (1977).
McCord et al., "Superoxide Dismutase—An Enzymic Function for Erythrocuprein", Biochemistry 492, p. 346.
McCord et al., Superoxide Dismutase an Enzymic Function for Erythrocuprein (Hemocuprein), The Journal of Biological Chemistry 244(22):6049-6055 (1969).
Milgrom et al., "Redox Behaviour of Phenolic Porphyrins in Basic Solutions: A Reappraisal", Free Rad. Res. 24 (1):19-29 (1996).
Milgrom, Facile Aerial Oxidation of a Porphyrin. Part 3. "Some Metal Complexes of meso-Tetrakis-(3,5-di-tbutyl-4-hydroxyphenyl)porphyrin", J. Chem. Soc. Perkin Trans. 11:71-79 (1988).
Moisy et al., "Catalytic Oxidation of 2,6-Di-Terbutylphenol by Molecular Oxygen Electroassisted by Poly(Pyrrole Manganese-Porphyrin)", New J. Chem. 13:511-514 (1989).
Naruta et al., "High Oxygen-Evolving Activity of Rigidly Linked Manganese (III) Porphyrin Dimers. A Functional Model of Manganese Catalase", J. Am. Chem. Soc. 113:3595-3596 (1991).
Oberley et al., "Anticancer activity of metal compounds with superoxide dismutase activity", Agents and Actions 15 (5/6):535-538 (1984).
Obst et al, "Helicobacter pylori causes DNA damage in gastric epithelial cells", Carcinogenesis 21(6):1111-1115 (2000).
European Search Report for European Application No. EP10011098 dated Jan. 14, 2011, 5 pages.
O'Hara et al., "Potentiation of radiation-induced cell kill by synthetic metalloporphyrins", Int. J. Radiat. Oncol. Biol. Phys. 16(4):1049-1052 (1989).
Ohkawa et al., "Assay for Lipid Peroxides in Animal Tissues by Thiobarbituric Acid Reaction", Analytical Biochemistry 95:351 (1979).
Oury et al., "Cold-induced Brain Edema in Mice", The Journal of Biological Chemistry 268(21):15394-15398 (1993).
Oury et al., "Establishment of Transgenic Mice Expressing Human Extracellular Superoxide Dismutase", American Review of Respiratory Disease 143(4):A515 (1991), International Conference Supplement Abstracts—No. 236.
Oury et al., "Immunocytochemical Localization of Extracellular Superoxide Dismutase in Human Lung", American Revew of Respiratory Disease 147(4):A713 (1993), International Conference Supplement Abstracts—No. 246.
Oury et al., "Transgenic Mice Superexpressing Human Extracellular Superoxide Dismutase Show Increased Resistance to Cold-induced Brain Edema, But are More Susceptible to Hyperbaric Oxygen", American Review of Respiratory Disease 145(4):A713, 1987.
Oury, Tim D., "Extracellular Superoxide Dismutase and Nitric Oxide: Transgenic and Immunocytochemical Studies", Dissertation submitted in partial fulfillment of the requirements for the degree of Doctor of Philosophy in the Department of Pathology in the, 1994.
Oury et al., "Extracellular superoxide dismutase, nitric oxide, and central nervous system 02 toxicity", Proc. Natl. Acad. Sci. USA 89:9715-9719 (1992).
Parge et al., "Atomic structures of wild-type and thermostable mutant recombinant human Cu,Zn superoxide dismutase", Proc. Natl. Acad. Sci. USA 89:6109-6113 (1992).
Pasternack et al., "Aggregation of Nickel(II), Copper (II), and Zinc(II) Derivatives of Water-Soluble Porphyrins", Inorganic Chemistry 12(11):2606-2610 (1973).
Pasternack et al., "Catalyst of the Disproportionation of Superoxide by Metalloporphyrins III", Journal of Inorganic Biochemistry 15:261-267 (1981).
Pasternack et al., "Catalyst of the Disproportionation of Superoxide by Metalloporphyrins", Journal of Inorganic Biochemistry 11:261-267 (1979).
Pasternack et al., "On the Aggregation of Meso-Substituted Water-Soluble Porphyrins", Journal of American Chemical Society 94(13):4511-4517 (1972).
Pasternack et al., "Superoxide Dismutase Activities of an Iron Porphyrin and Other Iron Complexes", Journal of the American Chemical Society 101(4):1026-1031 (1979).
Patel and Day, "Metalloporphyrin class of therapeutic catalytic antioxidants", TIPS Elsevier Trends Journal 20(9):359-364(1999).
Patel et al., "Requirement for Superoxide in Excitotoxic Cell Death", Neuron 16:345-355 (1996).
Peretz et al., "Chemical properties of water-soluble porphyrins 3. The reaction of superoxide radicals with some metalloporphyrins", Int. J. Radiat. Biol. 42(4):449-456 (1982).
Picker et al., "Cobalt(III) complexes of water soluble synthetic meso-substituted porphyrins as radiation sensitizers for oxic and hypoxic tumor cells", 8-Radiation 112:405 (1990) Abstract No. 112:73026d.
Pitie et al., "Oxidation at Carbon-1' of DNA Deoxyriboses by the Mn-TMPyP/KHSO5 System Results from a Cytochrome P-450-Type Hydroxylation Reaction", J. Am. Chem. Soc. 117:2935-2936 (1995).
Polson et al, "The Effect of Liver Transplantation in a 13-Year-Old Boy with Erythropoietic Protoporphyria", Transplantation 46(3):386-389 (1988).
Registry Copyright 2004 ACS on STN, Registry No. 138025-71-5, Entered STN: Dec. 21, 1991.
Richards et al, "Observation of a Stable Water-Soluble Lithium Porphyrin", Inorg. Chem. 35:1940-1944 (1996).
Robertson, Jr. et al, "Does Copper-D-Pehicillamine Catalyze the Disutatio of O2-?", Archives of Biochemistry and Biophysics 203(2) 830-831 (1980).
Rosenfeld et al., "Safety and pharmacokinetics of recombinant human superoxide dismutase administered intratracheally to premature neonates with respiratory distress syndrome", Pediatrics 97(Pt 1):811-817 (1996).
Ruoslahti et al., "Arg-Gly-Asp: A Versatile Cell Recognition Signal", Cell 44:517-518 (1986).
Sari et al., "Interaction of Cationic Porphyrins with DNA: Importance of the Number and Position of the Charges and Minimum Structural Requirements for Intercalation", Biochemistry 29:4205-4215 (1990).
Schlozer et al., "Reactivity of Unsubstituted Porphin", German version: Angew. Chem. 87:388 (1975).
Schneider et al., "Ligand-Porphyrin Complexes: Quantitative Evaluation of Stacking and Ionic Contributions", J. Org. Chem. 59:7464-7472 (1994).

(56) References Cited

OTHER PUBLICATIONS

Sharma et al., "Synthesis of amphiphilic 5-(4-N-alkylpyridiniumyl)-10,15,20-triphenylporphyrins and their aggregational properties in different solvent systems", Chemical Abstracts vol. 123, No. 1 (1995)—Abstract No. 9222q.

Sheldon, Chapter 1 in Metalloporphyrins in Catalytic Oxidations, Marcel Dekker, Inc. (1994).

Shimanovich et ai, "Mn(II)-Texaphyrin as a Catalyst for the Decomposition of Peroxynitrite", J. Am. Chem. Soc. 123:3613-3614 (2001).

Solomon et al., "Chemical properties of Water-Soluble Porphyrins. 2. The Reaction of Iron(III) Tetrakis(4 Nmethylpyridyl)porphyrin with the Superoxide Radical Dioxygen Couple", J. Phys. Chem. 86:1842-1849 (1982).

Song et al., "Anti-HIV activities of anionic metalloporphyrins and related compounds", Antiviral Chemistry and Chemotherapy 8(2):85 (1997).

Sonis et al, "AEOL 10150, a catalytic antioxidant, reduces the incidence and duration of radiation-induced oral mucositis in a hamster", European Journal of Cancer 37:S361 (2001)—Abstract.

Sorenson, John R.J., "Copper Chelates as Possible Active Forms of the Antiarthritic Agents", Journal of Medicinal Chemistry 19(1):135-148 (1976).

Spasojevic et al., "Manganese(III) complexes with porphyrins and related compounds as catalytic scavengers of superoxide", Inorganica Chimica Acta 317:230-242 (2001).

Stralin et al., "Effects of Oxidative Stress on Expression of Extracellular Superoxide Dismutase, CuZnSuperoxide Fibroblast", Biochem. J. 298:347-352 (1994).

Supplementary European Search Report for EP02739551 dated Aug. 5, 2009, 4 pages.

Szabo et ai, "Part I: Pathogenetic Role of Peroxynitrite in the Development of Diabetes and Diabetic Vascular Complications: Studies With FP15, A Novel Potent Peroxynitrite Decomposition Catalyst" Molecular Medicine 8(10):571-580 (2002).

Szabo et al., "Evaluation of the relative contribution of nitric oxide and peroxynitrite to the suppression of mitochondrial respiration in immunostimulated macrophages using a manganese mesoporphyrin superoxide dismutase mimetic and peroxynitrite scavenger", 1999.

Szabo et al., "Peroxynitrite is Involved in the Pathogenesis of the Vascular Contractile and Energetic Failure in Endotoxic Shock", Shock Society Meeting (1996).

Tjahjono et al., "Cationic porphyrins . . . ", Biochmica et Biophysica Acta 1472 (1999) 333-343. Note: Closest prior art.

Tsan, M-F., "Superoxide Dismutase and Pulmonary Oxygen Toxicity," XP-002074505, pp. 286-290, 1994.

Tsvetkov et al, "Infrared spectra of copper complexes of tetraphenylporphyrin", Izvestiya Vrvysshikh Uchebnykh Zavedenij, Khimiya I KhimicheskayaTekhnologiya 27(7):782-785 (1984)—English Abstract.

Vergeldt et al., "Intramolecular Interactions in the Ground and Excited State of Tetrakis(N-methylpyridyi) porphyrins", J. Phys. Chem. 99:4397-4405 (1995).

Vinogradov and Wilson, "Palladium catalyzed carbonylation of Br-substituted porphyrins", Tetrahedron Letters 39(49):8935-8938 (1998).

Vodzinskii et al., "Porphyrines and Their Derivatives. XX. Synthesis and Properties of 2-Nitro-5,10,15,20 tetraheterylporphyrins", Russian Journal of Organic Chemistry 34(6):882-885 (1998).

Walker et al, "Models of the cytochromes b, 5. EPR Studies of low-spin iron(III) tetraphenylporphyrins", Journal of the American Chemical Society 106(23):6888-6898 1984).

Wang et al, Structure of LB film of 5,10,15,20-tetra(p-ethoyycarbonphenyl)porphyrin, Yingyong Huaxue 10(21:87-88 (1993)—English Abstract.

Weinraub et al., "Chemical Properties of Water-Soluble Porphyrins. 1. Equilibria between Some Ligands and Iron (III) Tetrakis (4-N-methylpyridyl)porphyrin", J. Phys. Chem. 86:1839-1842 (1982).

Weinraub et al., "Chemical properties of water-soluble porphyrins. 5. Reactions of some manganese (III) porphyrins with the superoxide and other reducing radicals", Int. J. Radiat. Biol. 50(4):649-658 (1986) (Abs).

Weiss et al., "Evaluation of Activity of Putative Superoxide Dismutase Mimics", The Journal of Biological Chemistry 268(31):23049-23054 (1993).

Weiss et al., "Manganese-based Superoxide Dismutase Mimetics Inhibit Neutral Infiltration in Vivo", The Journal of Biological Chemistry 271(42):26149-26156 (1996).

Werringloer et al., "The Interaction of Divalent Copper and the Microsomal Electron Transport System", The Journal of Biological Chemistry, 254(23):11839-11846 (1979).

Wheelhouse et al., "Cationic Porphyrins as Telomerase Inhibitors; the Interaction of Tetra-(N-methyl-4pyridyl) porphine with Quadruplex DNA", J. Am. Chem. Soc. 120(13):3261-3262 (1998).

White et al, "A Highly Stereoselective Synthesis of Epothilone B", J. Org. Chem. 64:684-685 (1999).

Winkelman, James, "The Distribution of Tetraphenylporphinesulfonate in the Tumor-bearing Rat", Cancer Research 22:589-596 (1962).

Wolberg et al., "Electrocical and electron paramagnetic resonance studies of metalloporphyrins and their electrochemical oxidation products", Journal of the American 92(10):2982-90 (1970).

Yu and Su, "Electrocatalytic reduction of nitric oxide by water-soluble manganese porphyrins", Journal of Electroanalytical Chemistry 368:323-327 (1994).

Yue et al., "Carvedilol, a New Vasodilator and Beta Adrenoceptor Antagonist, is an Antioxidant and Free Radical Scavenger", The Journal of Pharmacology and Experimental Therapeutics 263:(1992).

Zahedi, "Semiempirical molecular orbital calculations of biliverdin: study of dynamics and energetics of the self association of a two-electron oxidation product", Theochem. 531:79-88 (2000).

Dorr et al., "Efficacy of sodium thiosulphate as a local antidote to mechlormethamine skin toxicity in the mouse," Cancer Chemother. Pharmacol. 1988;22(4):299-302 Abstract [On-line] [Found Mar. 25, 2013] (Found from database PubMed PMID: 3168143).

No Author, "Feature 'alkylating agents,'" [On-line] [Found Mar. 25, 2013] (Found from Internet: URL<ncbi.nlm.nih.gov/mesh/?term=alkylating+agents>).

Paromov et al., "Sulfur mustard toxicity following dermal exposure," J. Burns Wounds. 2007:7:e7(60-67) [On-line] [Found Mar. 25, 2013] (Found from Internet: URL<ncbi.nlm.nih.gov/pmc/articles/PMC2064967).

Russell et al., "Clinical management of casualties exposed to lung damaging agents: a critical review," Emerg. Med. J., 2006; 23:421-424 [On-line] [Found Mar. 25, 2013] (Found from Internet: URL<emjonline.com>).

Sandercock et al., "Mgmt deficiency alters the in vivo mutation spectrum of tissue exposed to the tobacco carcinogen 4-(methylnitrosamino)-1-(3-pyridyl)-1-butanone (NNK)," Carcinogenesis. Apr. 2008;29(4):886-74 [On-line] [Found Mar. 25, 2013] (Found from database PubMed PMID: 18281247).

Troyano et al., "Effect of glutathione depletion on antitumor drug toxicity (Apoptosis and Necrosis) in U-937 human promonocytic cells: the role of intracellular oxidation," Journal of Biological Chemistry, vol. 276, No. 50, pp. 47107-47115, 2001.

Office Action dated Aug. 20, 2013 in related Japanese Patent Application No. 2011-510747, filed May 26, 2009, 5 pages. English translation.

Office Action dated May 16, 2013 in related Russian Patent Application No. 2010152638, filed May 26, 2009, 3 pages, English translation..

Decision to Grant dated Sep. 2, 2013 in related Russian Patent Application No. 2010152638, filed May 26, 2009, 5 pages, English translation.

Bowler, Russell P. et al., "A catalytic antioxidant (AEOL 10150) attenuates expression on inflammatory genes in stroke", Free Radical Biology & Medicine, 33(8):1141-1152, 2002.

Chen, Ping et al., "Catalytic Metalloporphyrin Protects Against Paraquat Neurotoxicity in vivo", Biomedical and Environmental Sciences 21:233-238, 2008.

(56) References Cited

OTHER PUBLICATIONS

Crow, John P. et al., "Manganese Porphyrin Given at Symptom Onset Markedly Extends Survival of ALS Mice", *Annals of Neurology* 58(2):258-265, 2005.

Petri, Susanne et al., "Additive neuroprotective effects of a histone deacetylase inhibitor and a catalytic antioxidant in a transgenic mouse model of amyotrophic lateral sclerosis", *Neurobiology of Disease* 22:40-49, 2006.

Sheng, Huaxin et al., "Effects of metalloporphyrin catalytic antioxidants in experimental brain ischemia", *Free Radical Biology & Medicine* 33(7):947-961, 2002.

Extended Search Report dated Apr. 1, 2014 issued in European Application No. 14154916.2, 13 pages.

Japanese Office Action dated Mar. 4, 2014 issued in Japanese Application No. 2011-510747, English Translation, 7 pages.

Akdur et al., "Experimental Inhalation of Chlorine Gas Produced with a Different Method; Effects of N-Acetyl Cysteine on Acute Pulmonary Damage", *Toxicology Mechanisms and Methods*, 18:739-743, 2008.

Qin et al., "Effect of acute phosgene inhalation on antioxidant enzymes, nitric oxide and nitric-oxide synthase in rats.", *Zhonghua Lao Dong Wei Sheng Zhi Ye Bing Za Zhi* (Chinese Journal of Industrial Hygiene and Occupational Diseases), 22(3):200-202, 2004, [English Abstract retrieved online: http://www.ncbi.nlm.nih.gov/pubmed/15256156 on Jul. 2, 2014].

McGovern et al., "AEOL 10150: A novel therapeutic for rescue treatment after toxic gas lung injury", *Free Radical Biology & Medicine, Elsevier*, 50(5):602-608, 2011.

Canti, G. et al., "Hematoporphyrin derivative rescue from toxicity caused by chemotherapy or Yadiation in a murine leukemia model (L1210)", *Cancer Research* 44:1551-1556, Apr. 1984.

European Search Report for European Application No. EP09805313.5 dated Mar. 1, 2012, 14 pages.

Gould, Neal S. et al., "A role for mitochondrial oxidative stress in sulfur mustard analog 2-chloroethyl ethyl sulfide-induced lung cell injury and atioxidant protection", The Journal of Pharmacology and Experimental Therapeutics 328(3):732-739.

McClintock, Shannon D. et al., "Attenuation of half sulfur mustard gas-induced acute lung injury in rats", Journal of Applied Toxicology 26:126-131, 2006.

O'Neill, Heidi C. et al., "Catalytic antioxidant AEOL 10150 ameliorates 2-chloroethyl ethyl sulfide (CEES)-induced lung injury in rats", Free Radical Biology & Medicine 45(1):S89, 2008.

Holmes, W.W. et al. (Feb. 26, 2016, e-published Nov. 10, 2015). "Conceptual approaches for treatment of phosgene inhalation-induced lung injury," *Toxicol Lett* 244:8-20.

McElroy, C.S. et al. (Jan. 15, 2016, e-published Oct. 22, 2015). "Antioxidants as potential medical countermeasures for chemical warfare agents and toxic industrial chemicals," *Biochem Pharmacol* 100:1-11.

O'Neill, H.C. et al. (May 2010, e-published Feb. 4, 2010). "Treatment with the catalytic metalloporphyrin AEOL 10150 reduces inflammation and oxidative stress due to inhalation of the sulfur mustard analog 2-chloroethyl ethyl sulfide," *Free Radic Biol Med* 48(9): 1188-1196.

Tewari-Singh, N. et al. (Jul. 2014, e-published May 9, 2014). "Catalytic antioxidant AEOL 10150 treatment ameliorates sulfur mustard analog 2-chloroethyl ethyl sulfide-associated cutaneous toxic effects," *Free Radic Biol Med* 72:285-295.

\* cited by examiner

METHODS FOR TREATING INJURY ASSOCIATED WITH EXPOSURE TO AN ALKYLATING SPECIES

CROSS-REFERENCE TO RELATED APPLICATIONS

This application is a national stage application under 35 U.S.C. § 371 and claims the benefit of PCT Application No. PCT/US2009/045198 having an international filing date of May 26, 2009, which designated the United States, which PCT application claims priority to and benefit under 35 U.S.C. § 119(e) to U.S. Provisional Application Ser. No. 61/055,919, filed May 23, 2008, the disclosures of each of which are expressly incorporated by reference herein in their entirety.

GOVERNMENT SUPPORT

This invention was made with government support under Grant No. U54 ES015678 awarded by the National Institutes of Health. The government has certain rights in the invention.

BACKGROUND OF THE INVENTION

Bis (2-chloroethyl sulfide) or sulfur mustard (SM) was first synthesized in the late 1880s and since has been used as a warfare agent on a number of occasions. SM was first used in World War I and has been used in warfare as recently as the Iran-Iraq conflict of the late 1980s. Although SM is less of a threat in warfare as it once was, it still posses a threat to military and civilian personnel because of current concerns for its deployment in a terrorist attack.

Sulfur mustards are classic vesicating agents that mainly affect the skin, eyes, and respiratory system. Medical surveillance of individuals exposed to mustard gas in the early 1980's has documented a number of respiratory conditions including bronchiolitis obliterans, asthma, and lung fibrosis that can persist through out the victims' lifetime.

There is currently no known antidote for SM poisoning. Upon exposure, the best recourse is decontamination and supportive treatment. Decontamination of the skin is relatively straight forward and beneficial, whereas internal exposure such a inhalation of sulfur mustards is much more difficult to treat.

It can be seen from the foregoing discussion that there is a need for developing agents that are capable of attenuating, preventing, and/or rescuing organ injury from the deleterious effects resulting from exposure to alkylating agents (e.g., inhalation damage), such as sulfur mustards. The invention addresses these and other needs in the art.

BRIEF SUMMARY OF THE INVENTION

Provided herein are, inter alia, methods for rescuing or preventing organ injury following exposure to alkylating agents by using substituted porphyrins as the active agent or alkylating agent protectant, such as a mimetic of superoxide dismutase and/or catalase. The methodology of the invention may implemented as follows.

According to one aspect of the invention, a method of treating an injury associated with exposure to an alkylating agent in a subject includes administering to a subject in need thereof an effective amount of a compound of Formula

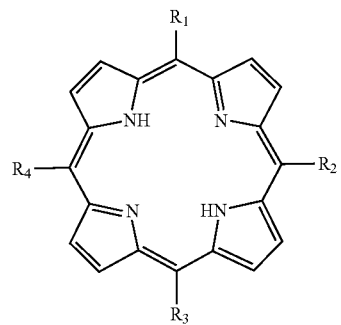

(I)

or a pharmaceutically acceptable salt thereof.

$R_1$, $R_2$, $R_3$, and $R_4$ may each independently be —H, —$CF_3$, —$CO_2R_8$,

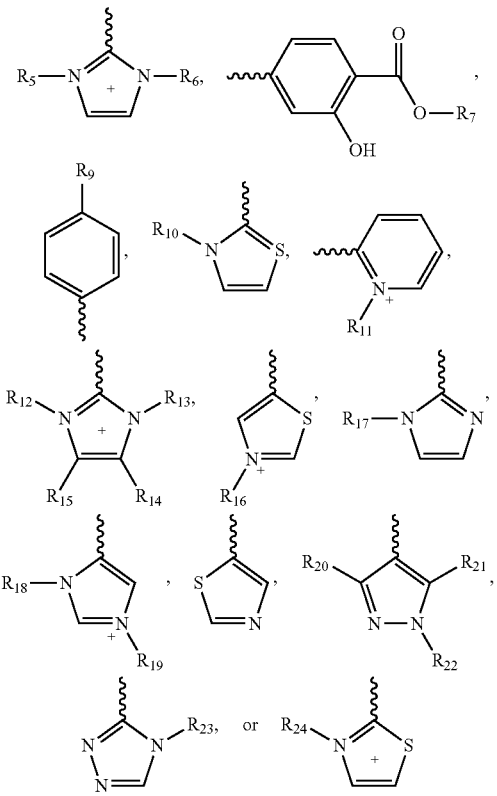

Each $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, and $R_{24}$ may be the same or different and may each independently be hydrogen, halogen, —CN, —$CF_3$, —OH, —$NH_2$, —COOH, —$COOR_{25}$, an unsubstituted or substituted alkyl, unsubstituted or substituted heteroalkyl, unsubstituted or substituted cycloalkyl, unsubstituted or substituted heterocycloalkyl, unsubstituted or substituted aryl, and an unsubstituted or substituted heteroaryl. $R_{25}$ may be an unsubstituted alkyl such as $C_{1-10}$ alkyl (e.g., $CH_3$).

The injury may be associated with an organ in the subject. Specifically, the organ may be skin, lungs, nose, esophagus, trachea, or bronchi. The alkylating agent may be a sulfur mustard, chlorine gas, phosgene, and 2-chloroethyl ethyl sulfide. Specifically, the alkylating agent is a sulfur mustard.

Exposure to the alkylating agent may produce mitochondrial dysfunction, which in turn may result in an increase in reactive oxygen species production or oxidative stress. In particular, exposure to the alkylating agent, relative to non-exposure to the alkylating agent causes an increase in lactate dehydrogenase (LDH) levels, an increase in IgM levels, a decrease of glutathione levels, and an increase in myleperoxidase levels.

The compound may be administered by inhalation administration, topical administration, intravenous administration, subcutaneous administration, intraperitoneal administration, and intramuscular administration. The compound may be administered to the subject within about 0.5 hours to about 48 hours after exposure to the alkylating agent. More specifically, the compound may be administered to the subject within about 1 hour to about 10 hours after exposure to the alkylating agent.

According to another aspect of the invention, a method of protecting a subject from the toxic effects associated with exposure to an alkylating agent includes administering to a subject in need thereof an effective amount of a compound of Formula $R_1$, $R_2$, $R_3$, and $R_4$ may each independently be —H, —$CF_3$, —$CO_2R_8$,

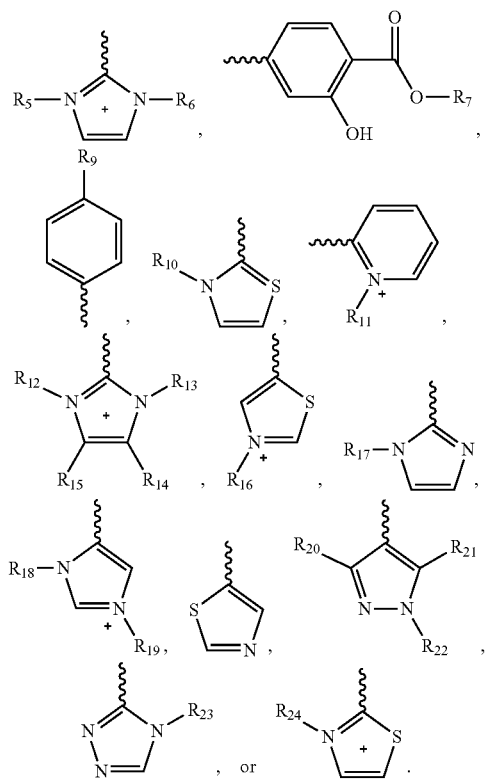

Each $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, and $R_{24}$ may be the same or different and may each independently be hydrogen, halogen, —CN, —$CF_3$, —OH, —$NH_2$, —COOH, —$COOR_{25}$, an unsubstituted or substituted alkyl, unsubstituted or substituted heteroalkyl, unsubstituted or substituted cycloalkyl, unsubstituted or substituted heterocycloalkyl, unsubstituted or substituted aryl, and unsubstituted or substituted heteroaryl. $R_{25}$ may be an unsubstituted alkyl such as $C_{1-10}$ alkyl (e.g., $CH_3$).

Additional features, advantages, and embodiments of the invention may be set forth or apparent from consideration of the following detailed description, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and various ways in which it may be practiced.

µM) was added 1 h after CEES exposure. Panel C, 16HBE cells were exposed similar as before except for 4 h. Mitochondrial membrane potential was determined using Rhodamine 123, where fluorescence is inversely correlated with mitochondrial membrane potential. Mean fluorescence was normalized to control levels with controls being 100%. Data represents mean±S.E.M., n=3 to 6; *, p<0.05; ***, p<0.001 compared with control values. Two-way ANOVA of AEOL 10150, p=0.0563; CEES, p=0.0033; interaction, p=0.042 (A); AEOL 10150, p=0.1073; CEES, p=0.0004; interaction, p=0.0001 (B); and AEOL 10150, p=0.2876; CEES, p=0.0007; interaction, p=0.0051 (C).

Figure 8:
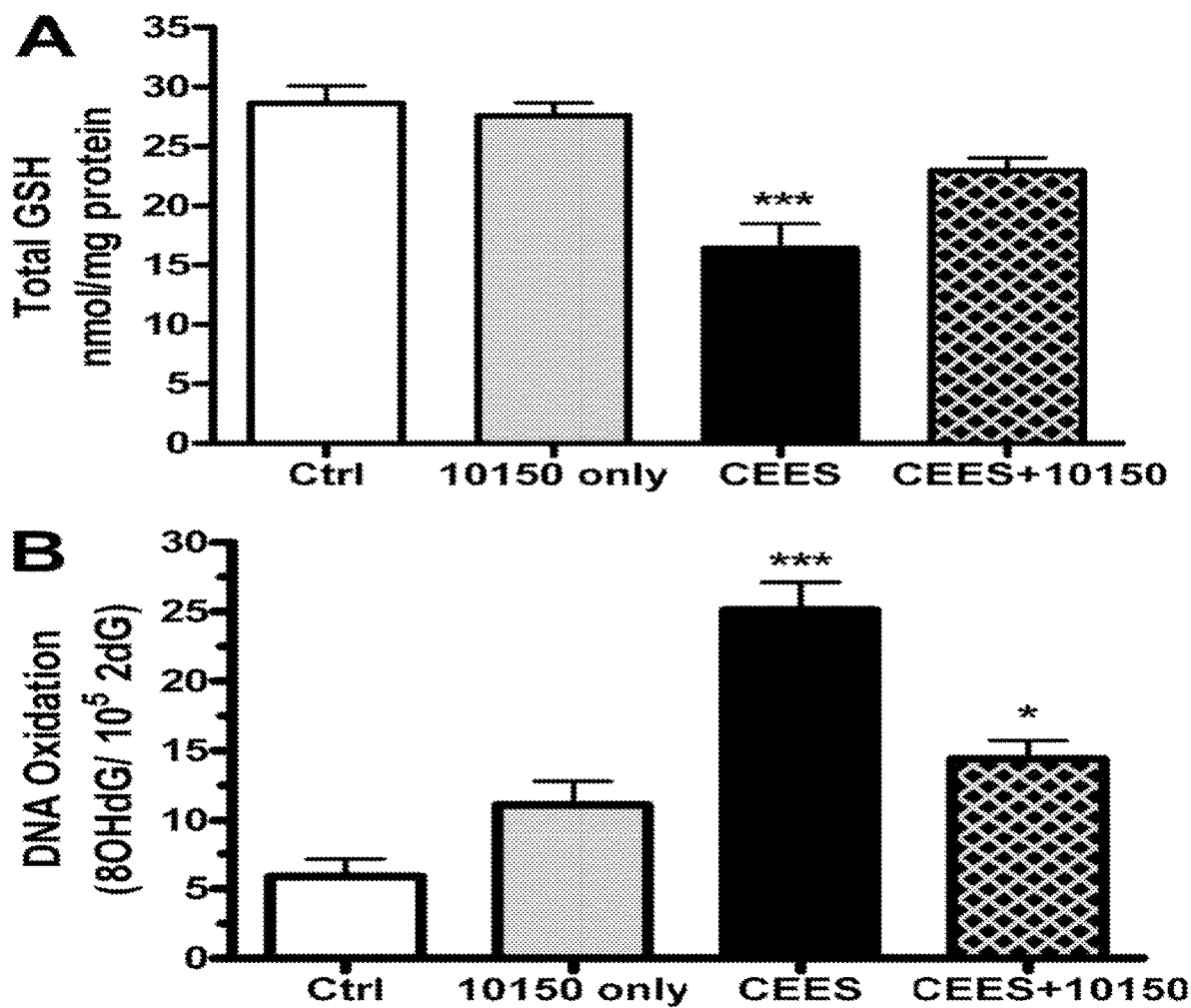

FIG. 8A-B are graphs showing the effects of CEES on markers of cellular oxidative stress and prevention by AEOL 10150 in 16 JIBE cells. Panel A: cells exposed to 900 µM CEES for 12 h had decreased total cellular GSH levels, and AEOL 10150 (50 µM) rescued this decrease when treated 1 h after CEES exposure. Total GSH levels were normalized to the amount of protein and expressed as nanomoles of GSH per milligram of protein. Panel B: CEES also increased the levels of the DNA oxidation marker 80 HdG, and AEOL 10150 (50 µM) post-CEES treatment decreased the levels of DNA oxidation. Data expressed as a ratio of 80 HdG per $10^5$ 2 dG. Data presented as mean±S.E.M., n=4 to 8; *, p<0.05; ***, p<0.001 compared with control levels. Panel A: two-way ANOVA of AEOL 10150, p=0.1444; CEES, p=0.0001; interaction, p=0.0481; Panel B: two-way ANOVA of AEOL 10150, p=0.1394; CEES, p=0.0001; interaction, p=0.0004.

FIG. 9A-D are graphs showing the effects of CEES on markers of injury, edema and inflammation and prevention by AEOL 10150 in rat lung. Panel A: the cytotoxicity marker lactate dehydrogenase (LDH) was measured spectrophotometrically. Panel B: protein levels which are a marker for edema were measured and was measured spectrophotometrically. Panel C: IgM, which is a marker of lung leak was measured by ELISA. Panel D: BAL cells, which are a marker of inflammation and hemorrhage were measure differential cytometry.

Figure 10:
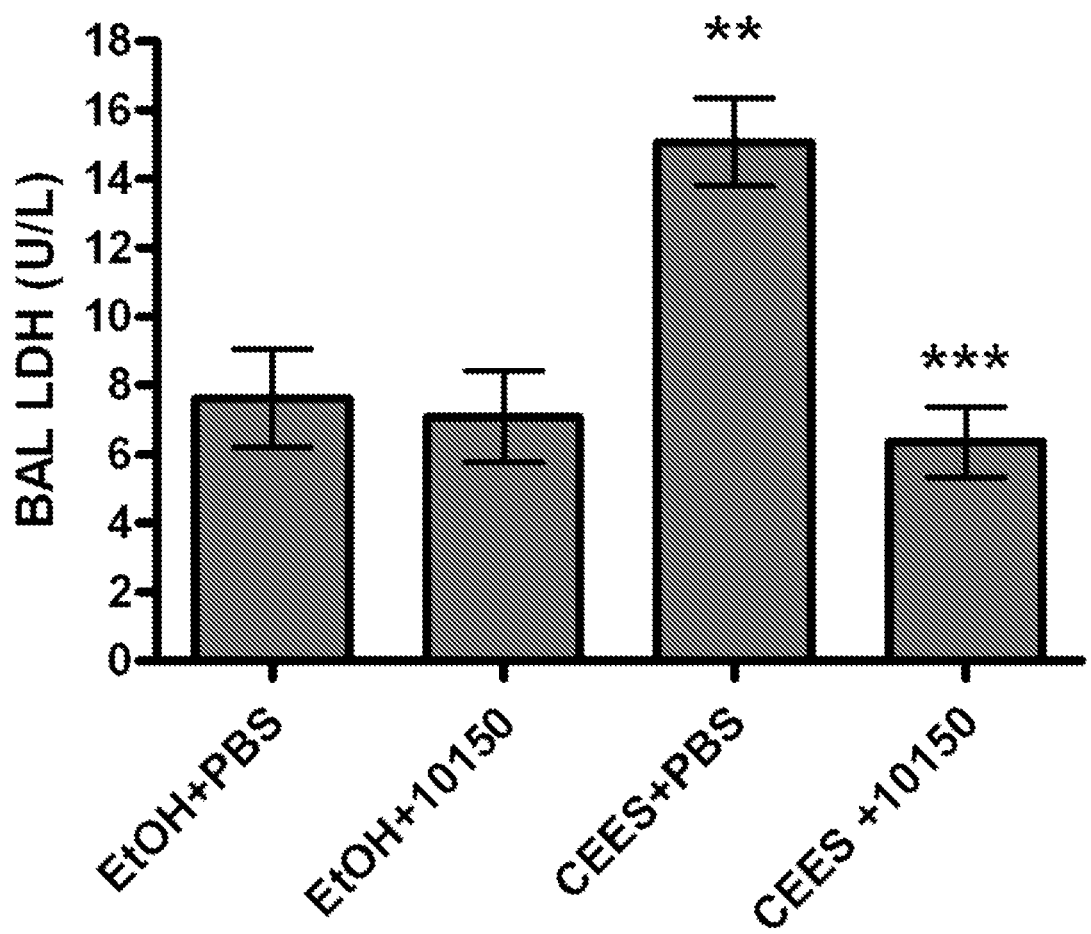

FIG. 10 is a graph showing LDH levels in the BAL were increased as a result of CEES inhalation; these levels were decreased to control values when AEOL 10150 was given following CEES. Levels of LDH in the BAL leak were significantly increased as a result of CEES, indicative of epithelial damage and thus leak from those damaged cells. Post exposure treatment with AEOL 10150 significantly decreased LDH leak from cells. Data are shown as mean±S.E.M., protein n–5 to 9. , p<0.01; *, p<0.001.

Figure 11:
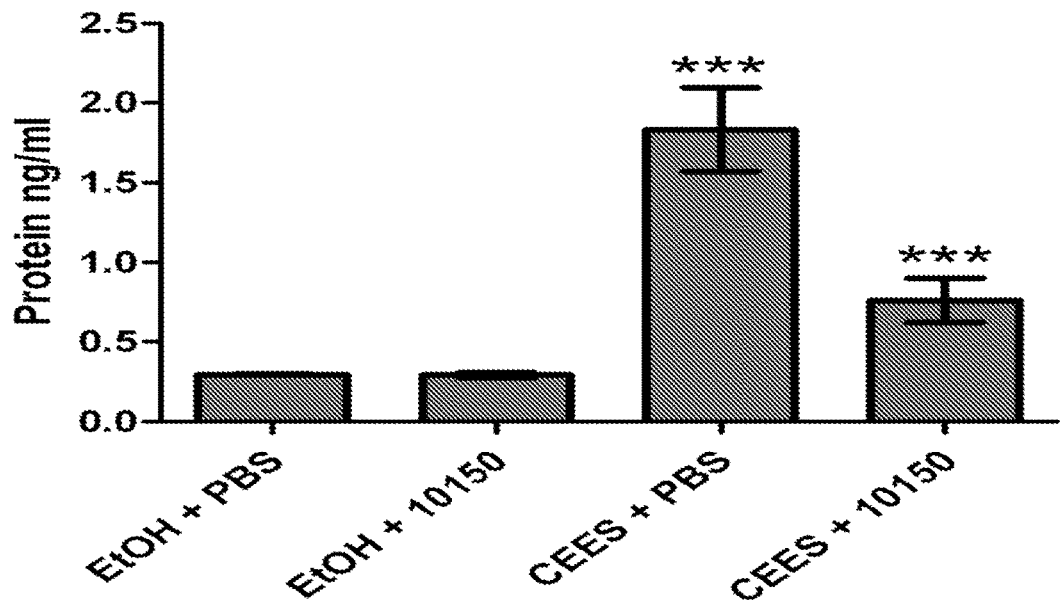
Figure 11:
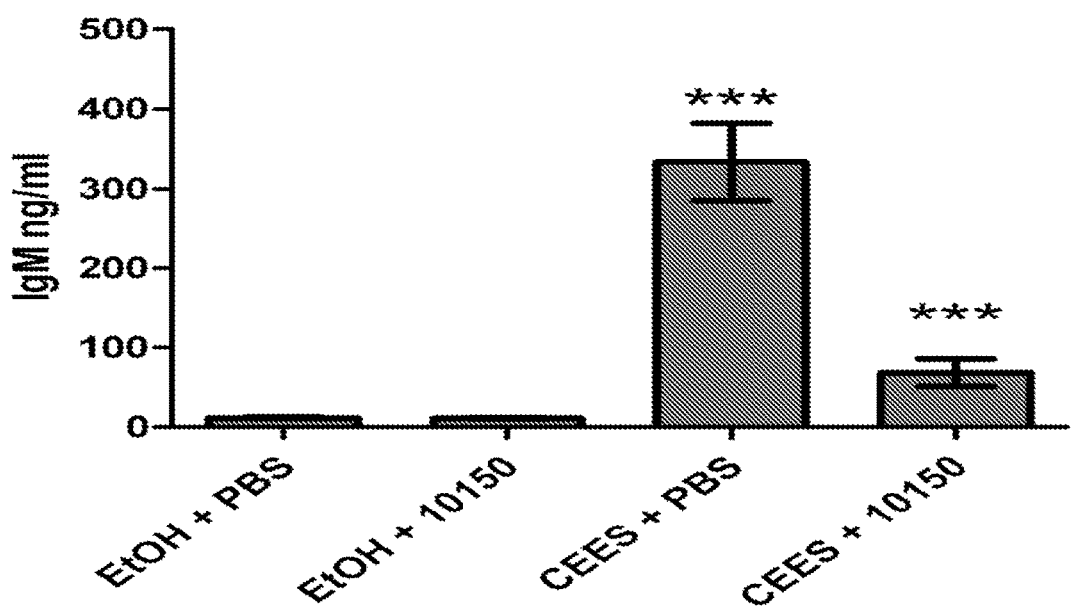

FIG. 11A-B are graphs showing the protective effect of AEOL 10150 on CEES-induced increases in BAL protein levels and BAL IgM. At 1 and 9 hours following CEES exposure, rats were treated with AEOL 10150 (5 mg/kg, SC). At 18 hours post exposure, rats were lavaged and levels of BAL protein and IgM were measured. Panel A: CEES exposure resulted in significant increases in BAL protein, while AEOL 10150 treatment with CEES exposure resulted in a significant decrease in protein in the BAL. Panel B: shows a significant increase in BAL IgM as a result of CEES exposure and a subsequent significant decrease in BAL 1 IgM with AEOL 10150 treatment following CEES exposure. Data are shown as mean±S.E.M., protein n=6 to 16. *, p<0.001. IgM n=6. *, p<0.001.

Figure 12:
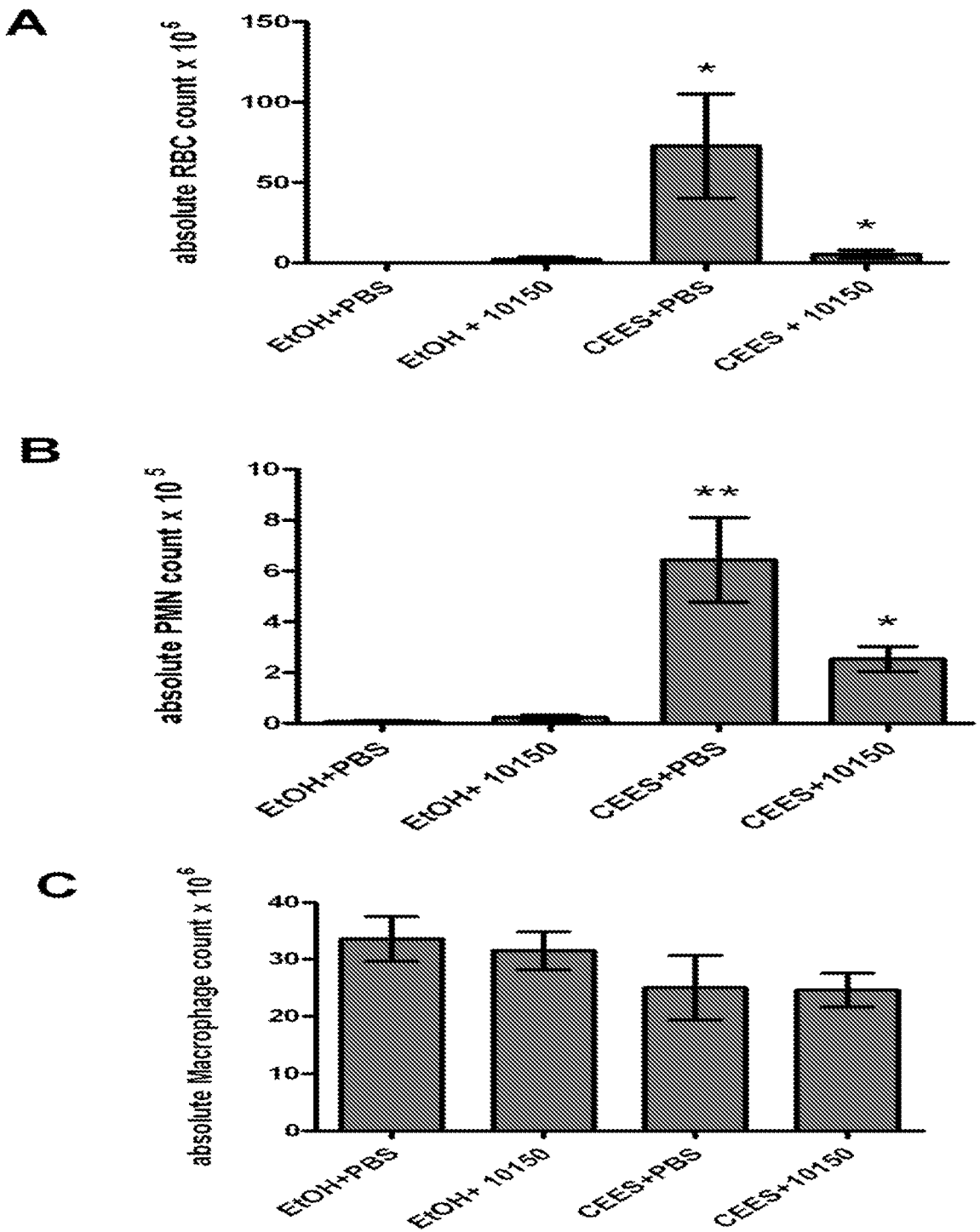

FIG. 12A-C are graphs showing that CEES inhalation resulted in increases in BAL RBCs and PMN; treatment with AEOL 10150 reduced BAL RBCs and PMN in BAL. Panel A: In EtOH+PBS or EtOH+AEOL 10150 treated rats, there were very low levels of RBCs. In the CEES+PBS group, rats had significantly increased RBCs in the BAL, indicative of hemorragic injury. Panel B: Neutrophils (polymorphonuclear cells, PMN) were also significantly increased in CEES+PBS treated rats as compared to both EtOH treatment groups. Treatment with AEOL 10150 following CEES resulted in significant decreases in PMN as compared to CEES+PBS. Macrophages were not significantly changed in any of the treatment groups. Data are mean±S.E.M., n=6 to 13. *, p=0.05; , p<0.01; *, p<0.001.

Figure 13:
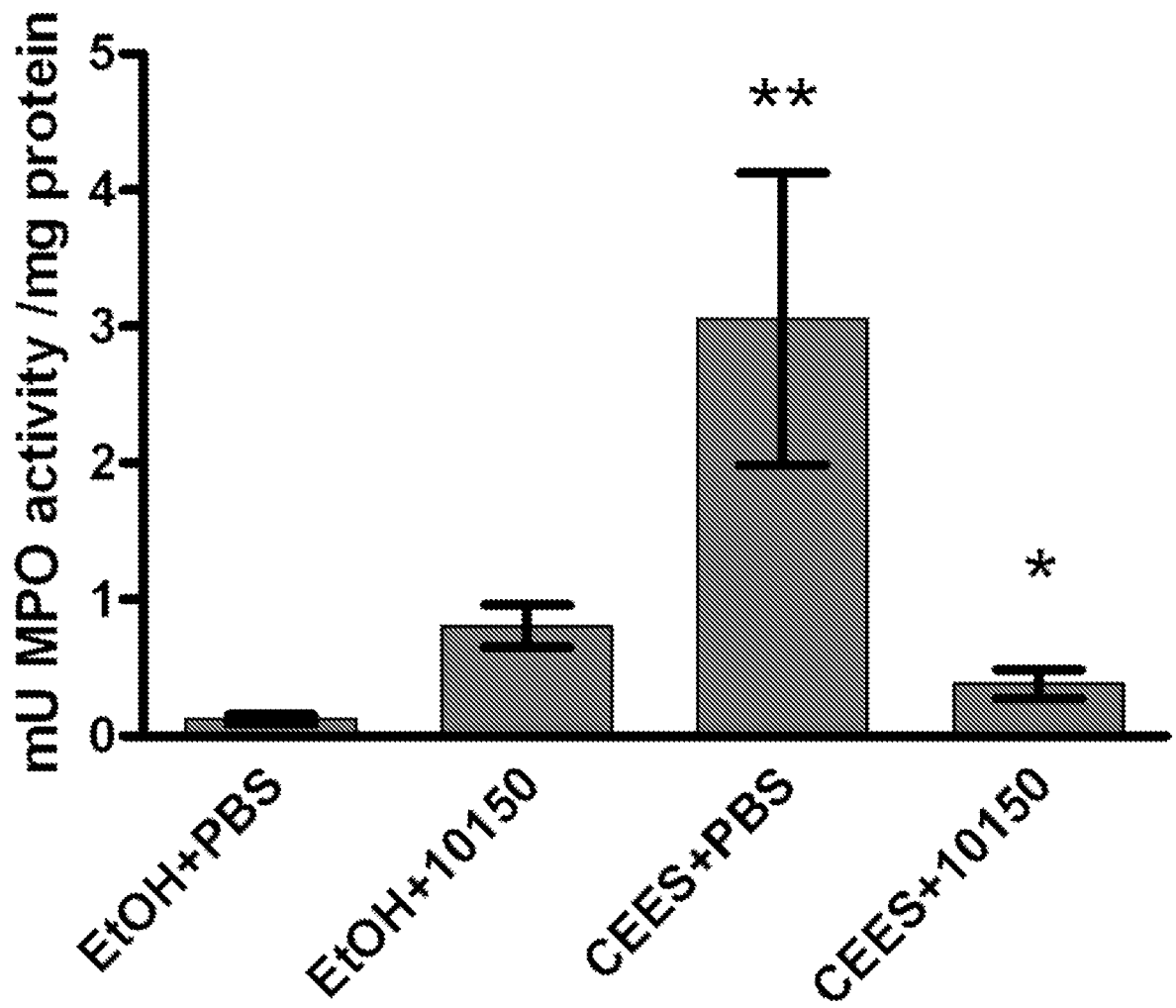

FIG. 13 is a graph showing that lung tissue myeloperoxidase levels were significantly increased in the CEES+PBS group; treatment with AEOL 10150 significantly decreased lung myeloperoxidase levels as compared to CEES+PBS. Lung tissue was perfused and snap frozen at the time of euthanization. Lung tissue was homogenized in HTAB buffer. Oxidation of tetramethylbenzidine (TMB) was followed for 3 minutes; this data was used to calculate a rate of change. An extinction coefficient for TMB of $3.9 \times 10^4$ $M^{-1}$ $cm^{-1}$ at 652 nm was used to calculate Units of peroxidase activity and activity was normalized to protein levels using the BCA protein assay. Data are shown as mean±S.E.M., n=6. *, p=0.05; **, p<0.01.

Figure 14:
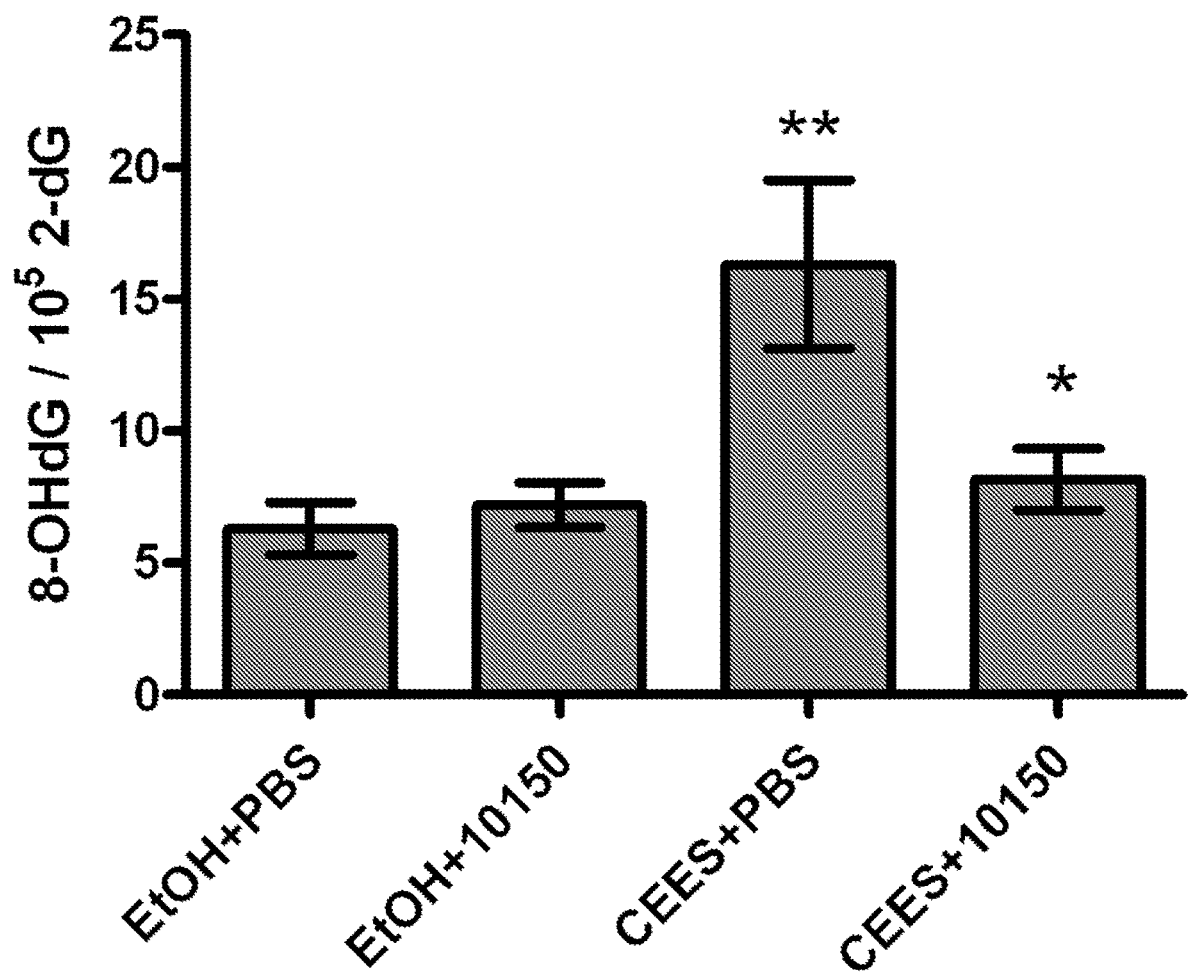

FIG. 14 is a graph showing that the DNA oxidation marker 8-hydroxydeoxyguanosine (8-OHdG) was significantly increased as a result of CEES inhalation; treatment with AEOL 10150 significantly decreased CEES-induced DNA oxidation. Data are shown as mean±S.E.M., n=12. *, p=0.05; **, p<0.01.

Figure 15:
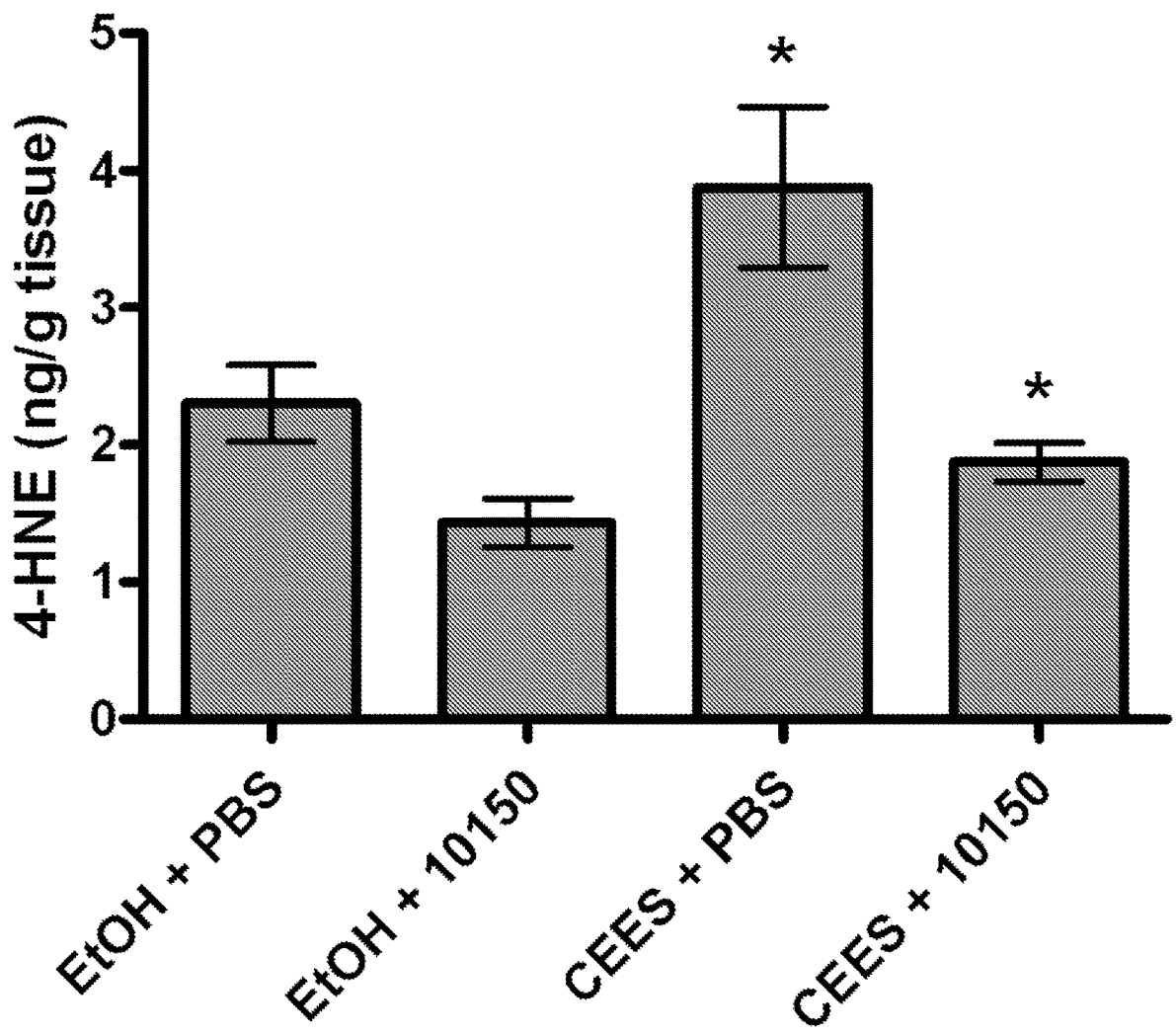

FIG. 15 is a graph showing that levels of the lipid peroxidation marker 4-hydroxynonenal (4-HNE) were elevated as a result of CEES exposure, treatment with AEOL 10150 significantly decreased levels of 4-HNE. Data are shown as mean±S.E.M., n=11 for EtOH+PBS and CEES+PBS, n=5 for EtOH+10150 and CEES+10150. *, p=0.05; **.

DETAILED DESCRIPTION OF THE INVENTION

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is be noted that as used herein and in the appended claims, the singular forms "a," "an," and "the" include the plural reference unless the context clearly dictates otherwise. Thus, for example, a reference to "a cell" is a reference to one or more cells and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law.

Accordingly, provided immediately below is a "Definition" section, where certain terms related to the invention are defined specifically for clarity, but all of the definitions are consistent with how a skilled artisan would understand these terms. Particular methods, devices, and materials are described, although any methods and materials similar or equivalent to those described herein can be used in the practice or testing of the invention. All references referred to herein are incorporated by reference herein in their entirety.

SM is sulfur mustard
CEES is 2-chloroethyl ethyl sulfide
SOD is superoxide dismutase
ROS is reactive oxygen species
RNS is reactive nitrogen species
GSH is glutathione
80 HdG is 8-hydroxydeoxyguanosine
MTT is 3-(4,5-Dimethylthiazol-2-yl)-2,5-diphenyltetrazolium bromide
ANOVA is analysis of variance
HBE is human bronchiolar epithelial cells
SAEC is human small airway epithelial cells
4-HNE is 4-hydroxynonenal "Alkylating agent," as used herein, generally refers to compounds containing alkyl groups that combine readily with other molecules. For example, alkylating agents typically contain alkyl groups that readily attach to other molecules thereby forming a covalent bond. This process may also be referred to as alkylation. Generally, alkylating agents can disrupt DNA function through different mechanisms, such as: (i) by alkylating DNA bases, thereby preventing DNA synthesis and RNA transcription, (ii) by mediating the formation of cross-bridges, bonds between atoms in the DNA strand, or (iii) by facilitating the mispairing of the nucleotides in the DNA strand thereby leading to mutations. Also, alkylating agents may initiate oxidative stress within the cells of the exposed organ system causing an overall decrease in intracellular glutathione (GSH) and increased DNA oxidation. Exposure to alkylating agents may cause blistering of the skin, damage to the eyes, and damage to the respiratory tract. Exposure to alkylating agents may also cause systemic toxic effects, such as nausea and vomiting, reduction in both leukocytes and erythrocytes, hemorrhagic tendencies, edema, depletion of glutathione, increased myleperoxidase (MPO), increased lactate dehydrogenase (LDH), and increased IgM. Alkylating agents include, without limitation, the nitrogen mustards, including mechlorethamine hydrochloride, chlorambucil, busulfan, cyclophosphamide, and the sulfur mustards including chlorine gas, phosgene, and 2-chloroethyl ethyl sulfide.

"Oxidation," as used herein, is a chemical reaction that transfers electrons from a substance to an oxidizing agent. Oxidation reactions may produce free radicals, which result in oxidative stress and may ultimately result in cell death.

"Reactive oxygen species," as used herein, generally refers to free radicals, reactive anions containing oxygen atoms, or molecules containing oxygen atoms that can either produce free radicals or are chemically activated by them. Reactive oxygen species may include, without limitation, superoxide radicals, hydrogen peroxide, peroxynitrite, lipid peroxides, hydroxyl radicals, thiyl radicals, superoxide anion, organic hydroperoxide, RO.alkoxy and ROO.peroxy radicals, and hypochlorous acid. The main source of reactive oxygen species (ROS) in vivo is aerobic respiration, although reactive oxygen species are also produced by peroxisomal b-oxidation of fatty acids, microsomal cytochrome P450 metabolism of xenobiotic compounds, stimulation of phagocytosis by pathogens or lipopolysacchrides, arginine metabolism, tissue specific enzymes. Accumulating oxidative damage may also affect the efficiency of mitochondria and further increase the rate of ROS production.

"Reactive nitrogen species," as used herein, generally refers to a family of biomolecules derived from nitric oxide (NO.) and may be produced in animals through the reaction of nitric oxide (NO.) with superoxide ($O_2^-$) to form peroxynitrite ($ONOO^-$). In general, reactive nitrogen species act together with reactive oxygen species to damage cells, resulting in nitrosative stress.

"Oxidative stress," as used herein, generally refers to cell damage caused by ROS. The primary damage to cells results from the ROS-induced alteration of macromolecules such as polyunsaturated fatty acids in membrane lipids, essential proteins and DNA. As described in U.S. Pat. No. 7,189,707, oxidative stress and ROS have been implicated in a number of disease states such as Alzheimer's disease, cancer, diabetes mellitus, and aging.

"Antioxidant," as used herein, generally refers to molecules or compounds with the capability to attenuate or prevent the oxidation of other molecules. Antioxidants may remove free radicals generated from oxidation reaction and inhibit other oxidation reactions by becoming oxidized themselves. Antioxidants may include reducing agents such as thiols or polyphenols. Additionally, antioxidants may include, without limitation, glutathione, vitamin C, vitamin E, catalase, superoxide dismutase, glutathione peroxidase, various other peroxidases, the substituted porphyrin compounds of the invention and any other molecule or compound that is capable of scavenging reactive oxygen species known in the art.

"Rescue," as used herein, is generally defined as counteracting, recovering, or conferring protection from the deleterious effects of reactive oxygen species and other free radicals in a subject, organ, tissue, cell, or biomolecule.

"Organ," as used herein, generally refers to a tissue that performs a specific function or group of functions within an organism. An exemplary list of organs includes lungs, heart, blood vessels, blood, salivary glands, esophagus, stomach, liver, gallbladder, pancreas, intestines, rectum, anus, endocrine glands such as hypothalamus, pituitary or pituitary gland, pineal body or pineal gland, thyroid, parathyroids, adrenals, skin, hair, nails, lymph, lymph nodes, tonsils, adenoids, thymus, spleen, muscles, brain, spinal cord, peripheral nerves, nerves, sex organs such as ovaries, fallopian tubes, uterus, vagina, mammary glands, testes, vas deferens, seminal vesicles, prostate, and penis, pharynx, larynx, trachea, bronchi, diaphragm, bones, cartilage, ligaments, tendons, kidneys, ureters, bladder, and urethra.

"Organ system," as used herein, generally refers to a group of related organs. Organ systems include, without limitation, circulatory system, digestive system, endocrine system, integumentary system, lymphatic system, muscular system, nervous system, reproductive system, respiratory system, skeletal system, and urinary system.

"Biomarker," as used herein, generally refers to an organic biomolecule which is differentially present in a sample taken from a subject of one phenotypic status (e.g., exposure to an alkylating agent) as compared with another phenotypic status (e.g., no exposure to an alkylating agent). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. As such, they are useful as markers for disease (diagnostics), therapeutic effectiveness of a drug (theranostics), and for drug toxicity.

"Subject," as used herein, includes individuals who require intervention or manipulation due to a exposure or potential exposure to an alkylating agent that can facilitate organ injury. Furthermore, the term "subject" includes non-human animals and humans.

"Active agent," as used herein, generally refers to any compound capable of inducing a change in the phenotype or genotype of a cell, tissue, organ, or organism when contacted with the cell, tissue, organ, or organism. For example, the compound may have the ability to scavenge ROS, prevent or attenuate oxidative stress, and protect organs and organ systems from injury due to exposure to an alkylating agent. The compound may include any substituted porphyrin compounds of the invention, such as a superoxide mimetic, a catalase mimetic or a mimetic having both features.

A "pharmaceutically acceptable carrier," as used herein, generally refers to pharmaceutical excipients, for example, pharmaceutically, physiologically, acceptable organic or inorganic carrier substances suitable for enteral or parenteral application that do not deleteriously react with the active agent.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two heteroatoms may be consecutive, such as, for example, —$CH_2$—NH—$OCH_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo," as used herein, means an oxygen that is double bonded to a carbon atom.

The term "alkylsulfonyl," as used herein, means a moiety having the formula —S(O$_2$)—R', where R' is an alkyl group as defined above. R' may have a specified number of carbons (e.g., "C$_1$-C$_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, and —NO$_2$ in a number ranging from zero to (2 m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

The term "pharmaceutically acceptable salts" is meant to include salts of the active compounds that are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the invention contain both basic and acidic functionalities that allow the compounds to be converted into either base or acid addition salts.

Thus, the compounds of the invention may exist as salts, such as with pharmaceutically acceptable acids. The invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the invention provides compounds in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms. In general, all physical forms are equivalent for the uses contemplated by the invention and are intended to be within the scope of the invention.

Certain compounds of the invention possess asymmetric carbon atoms (optical centers) or double bonds; the racemates, diastereomers, tautomers, geometric isomers, and individual isomers are encompassed within the scope of the invention. The compounds of the invention do not include those that are known in the art to be too unstable to synthesize and/or isolate.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the invention, whether radioactive or not, are encompassed within the scope of the invention.

The symbol "⌇⌇⌇" denotes the point of attachment of a chemical moiety to the remainder of a molecule or chemical formula.

"Effective dose" or "pharmaceutically effective dose," as used herein, generally refers to the amount of the substituted porphyrin(s) described herein that produces a desired therapeutic effect, such as counteracting the deleterious effects of alkylating agent exposure. The precise amount of the effective dose of a such a compound will yield the most effective results in terms of efficacy of treatment in a given subject will depend upon the activity, pharmacokinetics, pharmacodynamics, and bioavailability of a particular substituted porphyrin of the invention, physiological condition of the subject, the nature of the pharmaceutically acceptable carrier in a formulation, and a route of administration, among other potential factors. Those skilled in the clinical and pharmacological arts will be able to determine these factors through routine experimentation consisting of monitoring the subject and adjusting the dosage. Remington: The Science and Practice of Pharmacy (Gennaro ed. 20.sup.th edition, Williams & Wilkins PA, USA) (2000).

Methods

In one aspect, methods are provided for treating, rescuing and/or protecting organ and organ systems in a subject from the deleterious effects resulting from exposure to alkylating agents using substituted porphyrins. In one embodiment, a method for treating an injury associated with exposure to an alkylating agent in a subject includes administering to a subject in need thereof an effective amount of a compound described below (also referred to herein as a "substituted porphyrin"). In another embodiment, a method for protecting a subject from the toxic effects associated with exposure to an alkylating agent includes administering prophylactically to a subject in need thereof an effective amount of a compound described below (also referred to herein as a "substituted porphyrin"). In other embodiments, methods are provided for rescuing or protecting organ injury by administering substituted porphyrins such as substituted metalloporphyrins as the active agent of an alkylating agent protectant.

Compounds and compositions are provided herein that are suitable for such methods. The compounds include low molecular weight substituted porphyrins, including substituted metalloporphyrins. In some embodiments, the compounds are capable of mimicking the action of endogenous antioxidants, such as superoxide dismutase (SOD) and catalase.

Useful substituted porphyrins include any of the porphyrin compounds disclosed in U.S. Pat. No. 7,189,707 and U.S. Patent Publication No. 2007/0149498, the contents of each reference are expressly incorporated herein in their entirety. In some embodiments, the substituted porphyrin is an imidazolium porphyrins. In one embodiment, the compound useful in the methods provided herein has the formula:

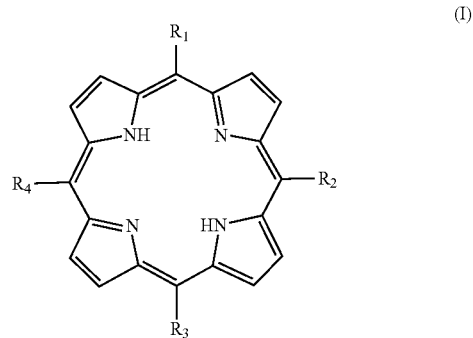

(I)

or a pharmaceutically acceptable salt thereof.

In Formula I, the substituted porphyrin may be bound to a metal. In formula II, below, M is a metal which may include manganese, iron, cobalt, copper, nickel, zinc, and ions thereof and may have the formula:

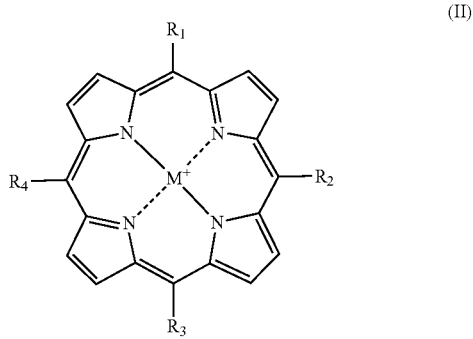

(II)

In a specific embodiment, the metal is manganese and has the formula:

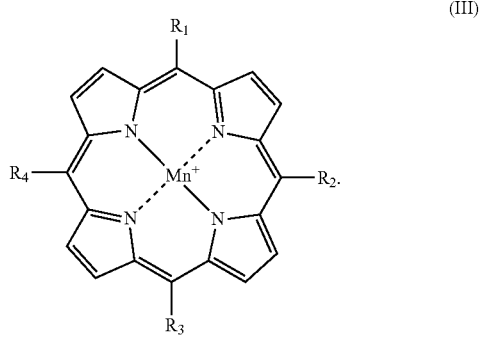

(III)

$R_1$, $R_2$, $R_3$, and $R_4$ may each independently be —H, —$CF_3$, —$CO_2R_8$,

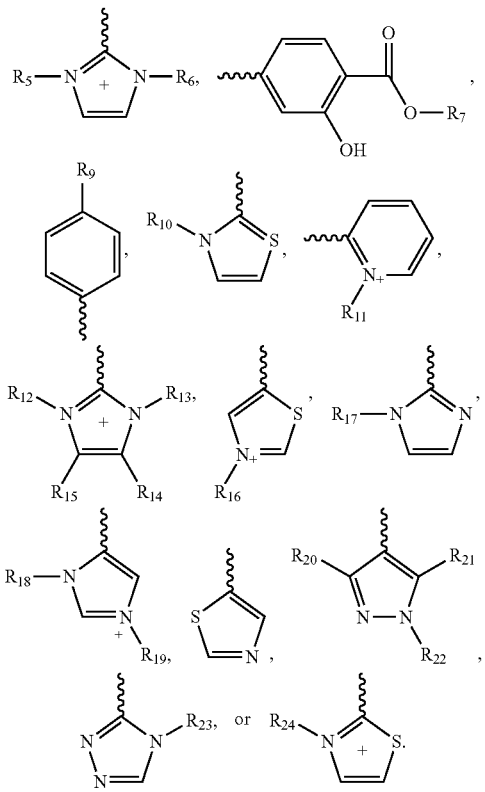

Where $R_1$, $R_2$, $R_3$, and $R_4$ contain a positive charge, one of skill will immediately recognize that an anionic compound or molecule will be present where the compound is in solution. Any applicable anionic compound are molecule may be used as a counterion to the positively charges substituents, including for example chloride, fluoride, sulfide, a sulfate, a carbonate, or a phosphate.

Each $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, and $R_{24}$ may be the same or different and may each independently be hydrogen, halogen, —CN, —$CF_3$, —OH, —$NH_2$, —COOH, —$COOR_{25}$, an unsubstituted or substituted alkyl, unsubstituted or substituted heteroalkyl, unsubstituted or substituted cycloalkyl, unsubstituted or substituted heterocycloalkyl, unsubstituted or substituted aryl, and an unsubstituted or substituted heteroaryl. $R_{25}$ may be an unsubstituted alkyl such as $C_{1-10}$ alkyl (e.g., $CH_3$). In some embodiments, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, and $R_{24}$ may each independently be hydrogen, halogen, —CN, —$CF_3$, —OH, —$NH_2$, —COOH, —$COOR_{25}$, substituted or unsubstituted $C_1$-$C_{10}$ (e.g., $C_1$-$C_6$) alkyl, substituted or unsubstituted 2 to 10 membered (e.g., 2 to 6 membered) heteroalkyl, substituted or unsubstituted $C_3$-$C_8$ (e.g., $C_5$-$C_7$) cycloalkyl, substituted or unsubstituted 3 to 8 membered (e.g., 3 to 6 membered) heterocycloalkyl, substituted or unsubstituted $C_5$-$C_8$ (e.g., $C_5$-$C_6$) aryl, or substituted or unsubstituted 5 to 8 membered (e.g., 5 to 6 membered) heteroaryl. In some embodiments, one or more of $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, and $R_{24}$ is unsubstituted. In one embodiment, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, and $R_{24}$ are independently hydrogen or a substituted or unsubstituted (e.g., $C_1$-$C_6$ or $C_1$-$C_3$) alkyl.

In one embodiment, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, and $R_{24}$, may independently be hydrogen, halogen, —CN, —$CF_3$, —OH, —$NH_2$, —COOH, —$COOR_{25}$, $R_{26}$-substituted or unsubstituted alkyl, $R_{26}$-substituted or unsubstituted heteroalkyl, $R_{26}$-substituted or unsubstituted cycloalkyl, $R_{26}$-substituted or unsubstituted heterocycloalkyl, $R_{26}$-substituted or unsubstituted aryl, or $R_{26}$-substituted or unsubstituted heteroaryl. $R_{26}$ is halogen, —CN, —$CF_3$, —OH, —$NH_2$, —COOH, —$COOR_{25}$, $R_{27}$-substituted or unsubstituted alkyl, $R_{27}$-substituted or unsubstituted heteroalkyl, $R_{27}$-substituted or unsubstituted cycloalkyl, $R_{27}$-substituted or unsubstituted heterocycloalkyl, $R_{27}$-substituted or unsubstituted aryl, or $R_{27}$-substituted or unsubstituted heteroaryl. In one embodiment, $R_{26}$ is halogen, —CN, —$CF_3$, —OH, —$NH_2$, —COOH, $R_{27}$-substituted or unsubstituted $C_1$-$C_{10}$ (e.g., $C_1$-$C_6$) alkyl, $R_{27}$-substituted or unsubstituted 2 to 10 membered (e.g., 2 to 6 membered) heteroalkyl, $R_{27}$-substituted or unsubstituted $C_3$-$C_8$ (e.g., $C_5$-$C_7$) cycloalkyl, $R_{27}$-substituted or unsubstituted 3 to 8 membered (e.g., 3 to 6 membered) heterocycloalkyl, $R_{27}$-substituted or unsubstituted $C_5$-$C_8$ (e.g., $C_5$-$C_6$) aryl, or $R_{27}$-substituted or unsubstituted 5 to 8 membered (e.g., 5 to 6 membered) heteroaryl.

$R_{27}$ is halogen, —CN, —$CF_3$, —OH, —$NH_2$, —COOH, —$COOR_{25}$, $R_{28}$-substituted or unsubstituted heteroalkyl, $R_{28}$-substituted or unsubstituted cycloalkyl, $R_{28}$-substituted or unsubstituted heterocycloalkyl, $R_{28}$-substituted or unsubstituted aryl, or $R_{28}$-substituted or unsubstituted heteroaryl. In one embodiment, $R_{27}$ is halogen, —CN, —$CF_3$, —OH, —$NH_2$, —COOH, $R_{28}$-substituted or unsubstituted $C_1$-$C_{10}$ (e.g., $C_1$-$C_6$) alkyl, $R_{28}$-substituted or unsubstituted 2 to 10 membered (e.g., 2 to 6 membered) heteroalkyl, $R_{28}$-substituted or unsubstituted $C_3$-$C_8$ (e.g., $C_5$-$C_7$) cycloalkyl, $R_{28}$-substituted or unsubstituted 3 to 8 membered (e.g., 3 to 6 membered) heterocycloalkyl, $R_{28}$-substituted or unsubstituted $C_5$-$C_8$ (e.g., $C_5$-$C_6$) aryl, or $R_{28}$-substituted or unsubstituted 5 to 8 membered (e.g., 5 to 6 membered) heteroaryl. $R_{28}$ is halogen, —CN, —$CF_3$, —OH, —$NH_2$, —COOH, —$COOR_{25}$, unsubstituted alkyl, unsubstituted heteroalkyl, unsubstituted cycloalkyl, unsubstituted heterocycloalkyl, unsubstituted aryl, or unsubstituted heteroaryl.

In one embodiment, $R_{26}$ and/or $R_{27}$ are substituted with a substituent group, a size-limited substituent group or a lower substituent group. In another embodiment, $R_{27}$ and $R_{28}$ are independently halogen, —CN, —$CF_3$, —OH, —$NH_2$, —COOH, $COOR_{25}$, unsubstituted $C_1$-$C_{10}$ (e.g., $C_1$-$C_6$) alkyl, unsubstituted 2 to 10 membered (e.g., 2 to 6 membered) heteroalkyl, unsubstituted $C_3$-$C_8$ (e.g., $C_5$-$C_7$) cycloalkyl, unsubstituted 3 to 8 membered (e.g., 3 to 6 membered) heterocycloalkyl, unsubstituted $C_5$-$C_8$ (e.g., $C_5$-$C_6$) aryl, or unsubstituted 5 to 8 membered (e.g., 5 to 6 membered) heteroaryl.

In a particular embodiment, each $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, and $R_{25}$ may be the same or different and may each independently be an alkyl, and particularly a $C_{1-20}$ alkyl, more particularly a $C_{1-30}$ alkyl, and even more particularly a $C_{1-4}$ alkyl, and even more particularly, a methyl, an ethyl, or a propyl.

In a more specific embodiment, $R_1$, $R_2$, $R_3$, and $R_4$ may each independently be
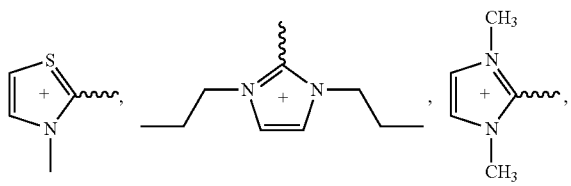
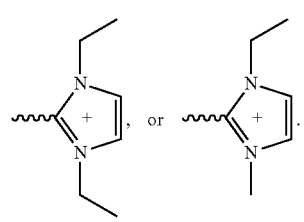
In a specific embodiment, the low molecule weight compound of the invention may have the formula:
(V)
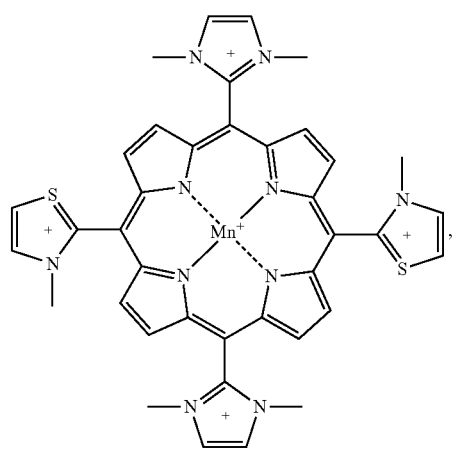
(IV)
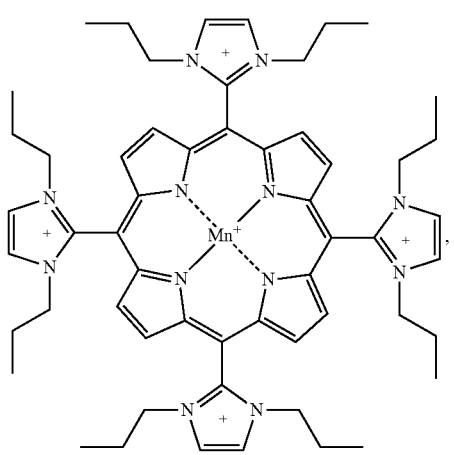
(VII)
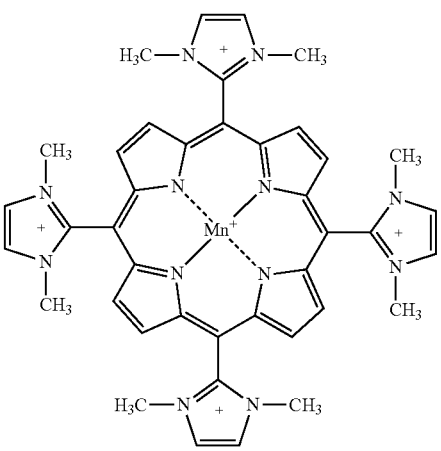
(VI)
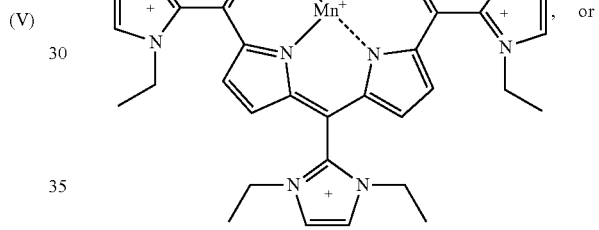
(VIII)
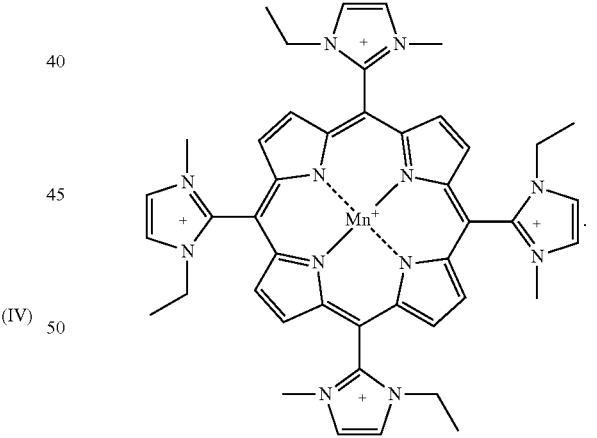
In another specific embodiment, $R_1$, $R_2$, $R_3$, and $R_4$ may each independently be
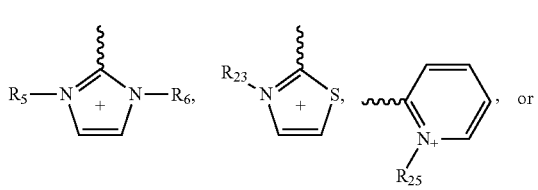

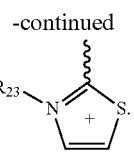

In another specific embodiment, $R_1$, $R_2$, $R_3$, and $R_4$ may each independently be

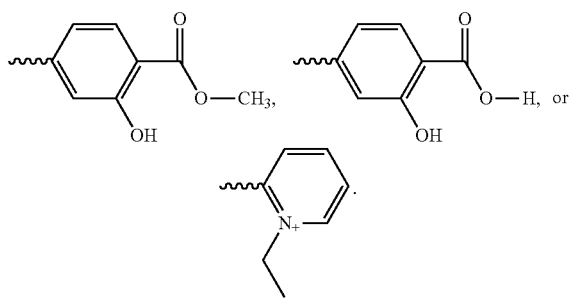

In a further specific embodiment, substituted porphyrin compounds of the invention may have the formula:

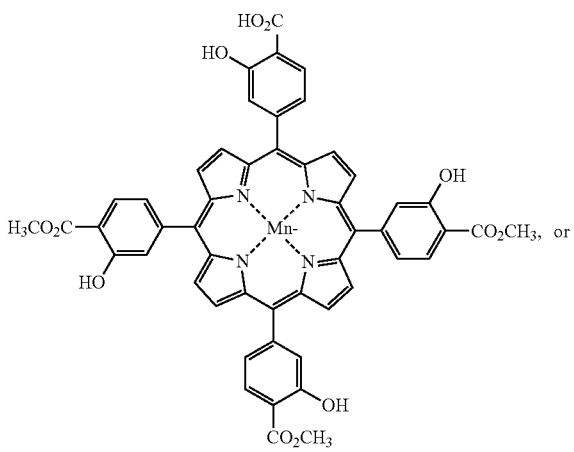

(IX)

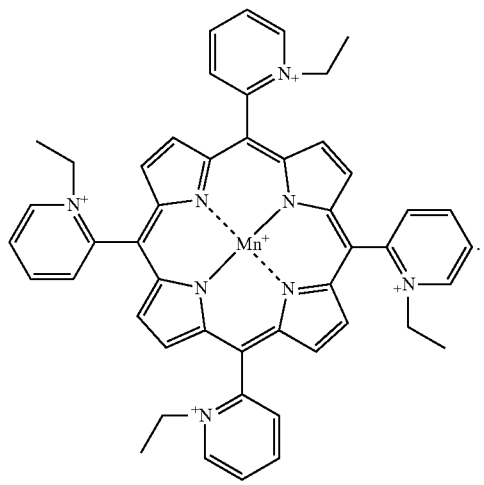

(X)

In some embodiments, each substituted group described in the compounds above (e.g., Formulae (I)-(X)) is substituted with at least one substituent group. More specifically, in some embodiments, each substituted alkyl, substituted heteroalkyl, substituted cycloalkyl, substituted heterocycloalkyl, substituted aryl, substituted heteroaryl, described in the compounds above (e.g., Formulae (I)-(X)) are substituted with at least one substituent group. In other embodiments, at least one or all of these groups are substituted with at least one size-limited substituent group. Alternatively, at least one or all of these groups are substituted with at least one lower substituent group.

In other embodiments of the compounds described above (e.g., Formulae (I)-(X)) each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

In another embodiment, the compounds are any one or all of the compounds set forth in Table 1, in the Examples section below.

Alkylating Agents

Alkylating agents contain alkyl groups that combine readily, typically through covalent bonding, with other molecules. Alkylating agents can disrupt DNA function by three mechanisms: (i) alkylating DNA bases, thereby preventing DNA synthesis and RNA transcription, (ii) mediating the formation of cross-bridges, bonds between atoms in the DNA strand, or (iii) facilitating the mis-pairing of the nucleotides in the DNA strand resulting in mutations in the DNA strand. Also, alkylating agents may initiate oxidative stress within the cells of the exposed organ system causing an overall decrease in intracellular glutathione (GSH) and increased DNA oxidation.

Alkylating agents include, without limitation, the nitrogen mustards, such as mechlorethamine hydrochloride, chlorambucil, busulfan, cyclophosphamide, and the sulfur mustards such as chlorine gas, phosgene, and 2-chloroethyl ethyl sulfide (CEES). Exposure to alkylating agents may cause blistering of the skin, damage to the eyes, and damage to the respiratory tract. Exposure to alkylating agents may also cause systemic toxic effects, such as nausea and vomiting, hemorrhagic tendencies, edema, and a reduction in both leukocytes and erythrocytes.

Figure 1:
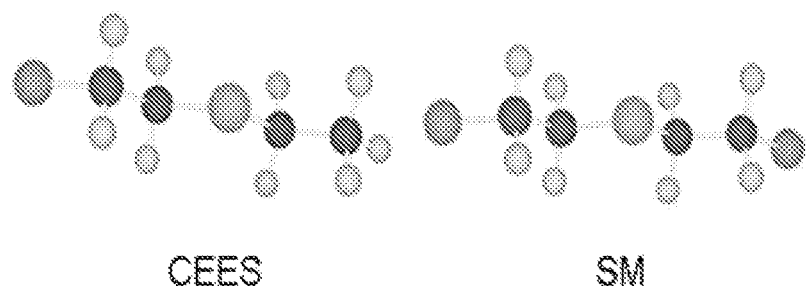
FIG. 1 shows the structures of bis(2-chloroethyl sulfide), known as SM, and its analog chloroethyl ethyl sulfide (GEES).

Sulfur mustard (2,2'-dichloro diethyl sulfide) is a known potent vesicating agent and inhalation results in apoptosis and necrosis of the airway epithelium, inflammation, edema, and pseudomembrane formation. 2-chloroethyl ethyl sulfide (CEES, half mustard) is a monofunctional analog of SM that can be utilized to elucidate the mechanisms of injury and as an initial screening of therapeutics. Both SM and CEES (FIG. 1) are alkylating agents capable of binding macromolecules including proteins, DNA and lipids.

Oxidative stress plays a significant role in SM/CEES mediated damage. For example, exposure to CEES causes an imbalance in production of ROS/RNS and antioxidant defenses in favor of the former. There are many factors that contribute to the increase in ROS following SM/CEES exposure. For example, exposure to SM/CEES facilitates the proliferation of inflammatory cells such as polymorphonuclear leukocytes (PMN), which in turn produces oxidants, including superoxide and hypochlorous acid (HOCl). Furthermore, exposure to CEES also results mitochrondrial dysfunction which further drives increased ROS production, and ultimately, oxidative stress.

As discussed above, following exposure to SM/CEES, there is irreparable damage to the respiratory tract such as apoptosis and necrosis of the airway epithelium. However, in certain embodiments of the invention, administration of the substituted porphyrins of the invention subsequent to alkylating agent exposure, have been shown to significantly improve the outcome. For example, administration of the substituted porphyrins of the invention following CEES exposure have been shown to rescue lung cells and airway cells from alkylating agent-induced toxicity, prevent alkylating agent-mediated ROS and dysfunction, and alkylating agent-induced oxidative stress. In further embodiments, the substituted porphyrins of the invention have been shown to reduce alkylating agent-induced cytotoxicity, reduce alkylating agent-induced increases of protein and IgM in the lung, reduce levels of RBCs and inflammatory cells in the lung, decrease tissue accumulation of PMN, and prevent alkylating agent-induced oxidative stress.

Biomarkers of Alkylating Agents

A specific embodiment of the invention is directed to biomarkers that are characteristic of alkylating agent exposure. The biomarkers of alkylating agent exposure may include ROS such as superoxide radicals, hydrogen peroxide, peroxynitrite, lipid peroxides, hydroxyl radicals, thiyl radicals, superoxide anion, organic hydroperoxide, RO.alkoxy and ROO.peroxy radicals, and hypochlorous acid, reactive nitrogen compounds, and compounds indicative of oxidative stress, such a lipid peroxidation products.

In a specific embodiment, biomarkers characteristic of exposure to the half mustard gas, CEES, include glutathione, myleperoxidase (MPO), lactate dehydrogenase (LDH), IgM, 8-OHdG, 4-HNE, and increase in extracellular proteins which are associated with edema. Specifically, following CEES exposure, there is a depletion of glutathione, increased levels of myleperoxidase (MPO), increased levels of LDH, increased levels of IgM, increased levels in markers of oxidized DNA such as 8-oxo-2 dG, and increased levels in markers of lipid oxidarion such as 4-hydroxynonenal (4HNE). In certain aspects, the presence of increased LDH levels may be indicative of increased cytotoxicity, the presence of increased protein levels may be indicative of epithelial cell death, the presence of increased IgM levels may be indicative of increased vascular permeability, and the presence of MPO may be indicative of inflammatory response. Oxidative stress occurs when oxidant production exceeds antioxidant defense. Thus, one marker of oxidative damage is DNA oxidation, which can be measured by the formation of 8O-HdG. Another marker of oxidative damage is the formation of lipid peroxidation products including 4-hydroxynonenal (4-HNE).

In another embodiment of the invention, a biomarker profile following alkylating agent exposure may be used for determining therapeutic efficacy or toxicity of a compound. If the compound has a pharmaceutical impact on the subject, organ or cell following exposure to the alkylating agent, the phenotype (e.g., the pattern or profile) of the biomarkers changes towards a non-exposure profile. For example, glutathione is depleted following alkylating agent exposure and lactate dehydrogenase (LDH) is increased following alkylating agent exposure. Therefore, one can follow the course of the amounts of these biomarkers in the subject, organ, or cell during the course of treatment. Accordingly, this method involves measuring one or more biomarkers upon exposure to the alkylating agent. Methods for measuring the specific biomarkers are a matter of routine experimentation and are known by those of skill in the art and are described in U.S. Pat. No. 7,189,707, which is expressly incorporated by reference in its entirety herein.

Formulations

In another embodiment, the invention provides pharmaceutical compositions comprising a low molecular weight substituted porphyrin compound of the invention or a low molecular weight substituted porphyrin in combination with a pharmaceutically acceptable excipient (e.g., carrier). Suitable pharmaceutically acceptable carriers include water, salt solutions (such as Ringer's solution), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be co-administered to the subject. Co-administration is meant to include simultaneous or sequential administration of the compounds individually or in combination (more than one compound). The preparations can also be combined, when desired, with other active substances (e.g. antioxidants). For example, the compounds of the invention may be co-administered with glutathione, vitamin C, vitamin E, catalase, superoxide dismutase, glutathione peroxidase, various other peroxidases, and any other molecule or compound that is capable of scavenging reactive oxygen species known by those skilled in the art.

The substituted porphyrin compounds of the invention may be prepared and administered in a wide variety of oral, parenteral, and topical dosage forms. Thus, the compounds of the invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the invention can be administered transdermally. It is also envisioned that multiple routes of administration (e.g., intramuscular, oral, transdermal) can be used to administer the compounds of the invention. Accordingly, the invention also provides pharmaceutical compositions comprising a pharmaceutically acceptable carrier or excipient and one or more compounds of the invention.

For preparing pharmaceutical compositions from the compounds of the invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a Mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the invention include those described, for example, in Pharmaceutical Sciences (17th Ed., Mack Pub. Co., Easton, Pa.) and WO 96/05309, the disclosures of both of which are hereby incorporated by reference.

Aqueous solutions suitable for oral use can be prepared by dissolving the active component in water and adding suitable colorants, flavors, stabilizers; and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Dosages

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60; and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The dosage of the composition of the invention to be administered can be determined without undue experimentation and will be dependent upon various factors including the nature of the active agent (whether metal bound or metal free), the route of administration, the subject, and the result sought to be achieved. A suitable dosage of the compound to be administered IV or topically can be expected to be in the range of about 0.01 to about 50 mg/kg/day, and more particularly, in the range of about 0.1 mg/kg/day to about 10 mg/kg/day. For aerosol administration, it is expected that the dose will be in the range of about 0.001 mg/kg/day to about 5/. Mg/kg/day, and more specifically, in the range of about 0.01 mg/kg/day to about 1 mg/kg/day. Suitable doses of the compounds will vary, for example, with the compound and with the result sought.

In certain embodiments, the compounds of the invention may be administered prophylactically to serve as a protectant against exposure to an alkylating agent. The compounds may be administered in the dosage amounts specified above about 1 hour to about 48 hours prior to alkylating agent exposure. In specific embodiments, the compound of the invention may be administered about 1 to about 24 hours, more specifically, about 1 to about 12 hours, more specifically about 1 to about 6 hours, and even more specifically, about 1 to about 6 hours prior to alkylating agent exposure.

In further embodiments, the compound of the invention may be administered in the dosage amounts specified above about 1 to about 48 hours following exposure to an alkylating agent. In specific embodiments, the compound of the invention may be administered about 1 to about 24 hours, more specifically, about 1 to about 12 hours, more specifically about 1 to about 6 hours, and even more specifically, about 1 to about 6 hours following alkylating agent exposure.

For any compound described herein, the therapeutically effective amount can be initially determined from cell culture assays. Target concentrations will be those concentrations of active compound(s) that are capable of counteracting the effects of the alkylating agent, by monitoring the presence, absence, or alteration in levels of the biomarkers indicative of alkylating agent exposure, such as glutathione, LDH, IgM, and 8O-HdG, for example. Methods for measuring the levels of such compounds is known by those of skill in the art and is matter of routine experimentation.

Therapeutically effective amounts for use in humans may be determined from animal models. For example, a dose for humans can be formulated to achieve a concentration that has been found to be effective in animals. The dosage in humans can be adjusted by monitoring the levels of the biomarkers indicative of exposure to an alkylating agent and adjusting the dosage upwards or downwards.

Dosages may be varied depending upon the requirements of the patient and the compound being employed. The dose administered to a patient, in the context of the invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compound effective for the particular indication being treated. This will provide a therapeutic regimen that is commensurate with the severity of the individual's reaction following exposure to the alkylating agent.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

Without further elaboration, it is believed that one skilled in the art using the preceding description can utilize the invention to the fullest extent. The following examples are illustrative only, and not limiting of the disclosure in any way whatsoever.

EXAMPLES

For the purpose of the following specific examples, the compounds of Formulas III-IX described in the detailed description above, will be designated as indicated in Table 1, immediately below:

TABLE 1

| Compound of Formula | AEOL No. Designation |
| --- | --- |
| IV | AEOL 10153 |
| V | AEOL 10158 |
| VI | AEOL 10123 |

TABLE 1-continued

| Compound of Formula | AEOL No. Designation |
| --- | --- |
| VII | AEOL 10150 |
| VIII | AEOL 10151 |
| IX | AEOL 10303 |
| X | AEOL 10113 |

Specific Example 1

CEES-Induced Airway Epithelial Cell Injury

Figure 2:
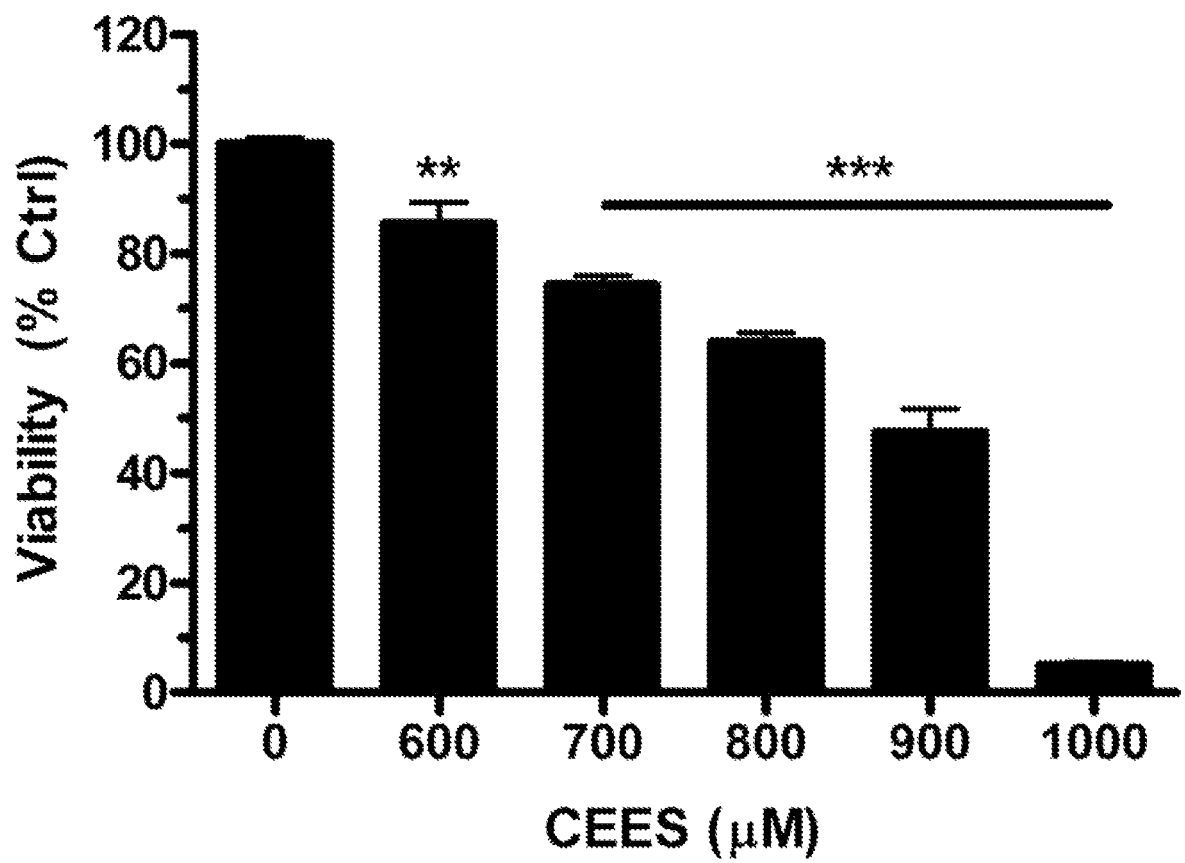
FIG. 2 is a graph showing that CEES exposure caused a concentration-dependent injury of human airway epithelial cells. Human lung 16HBE cells were grown to approximately 90% confluence and treated with concentrations of CEES ranging from 600 to 1000 μM for 24 h. Cell viability decreased in a dose-dependent manner as measured by quantifying calcein AM fluorescence. Data represented as mean±S.E.M., n=4 where control group fluorescence was defined as 100% viability.

Human lung 16HBE cells were grown to approximately 90% confluence and treated with increasing concentrations of CEES, ranging from about 600 to about 000 μM. Cell viability was determined by measuring the fluorescence of calcein AM and was found to decrease in a dose-dependent manner from 80% with the 600 μM CEES to below 10% with 1000 μM CEES (FIG. 2). 900 μM CEES was used as the optimal dose to carry out the cytoprotection studies because it provided enough cell injury (about 50%) for potential therapeutics to demonstrate efficacy and the most consistent cell injury response in the two cell systems. Because of observed increased resistance of SAE cells to CEES toxicity as seen with 16HBE cells, these exposures were prolonged to 48 h in the SAE cells to provide similar injury responses for comparison of antioxidant protective effects between cell systems.

Specific Example 2

Delayed Increase in Mitochondrial ROS and Dysfunction with CEES Exposure

As discussed above, mitochondria are a major source of cellular ROS production. Both SAE and 16HBE cells were exposed to 900 μM CEES for 2, 4, 6, 8, 12, 24, and 48 h, after which the cells were incubated with MitoSOX (MitoSOX is a mitochrondrially targeted ROS probe) and fluorescence was measured using flow cytometry. CEES exposure increased ROS levels that peaked at 12 h, and this time-dependent increase was seen in both SAE (FIG. 3A) and 16HBE (FIG. 3B) cells. As a consequence, further exposure studies measuring markers of cellular stress were examined after 12 h of exposure.

Figure 3:
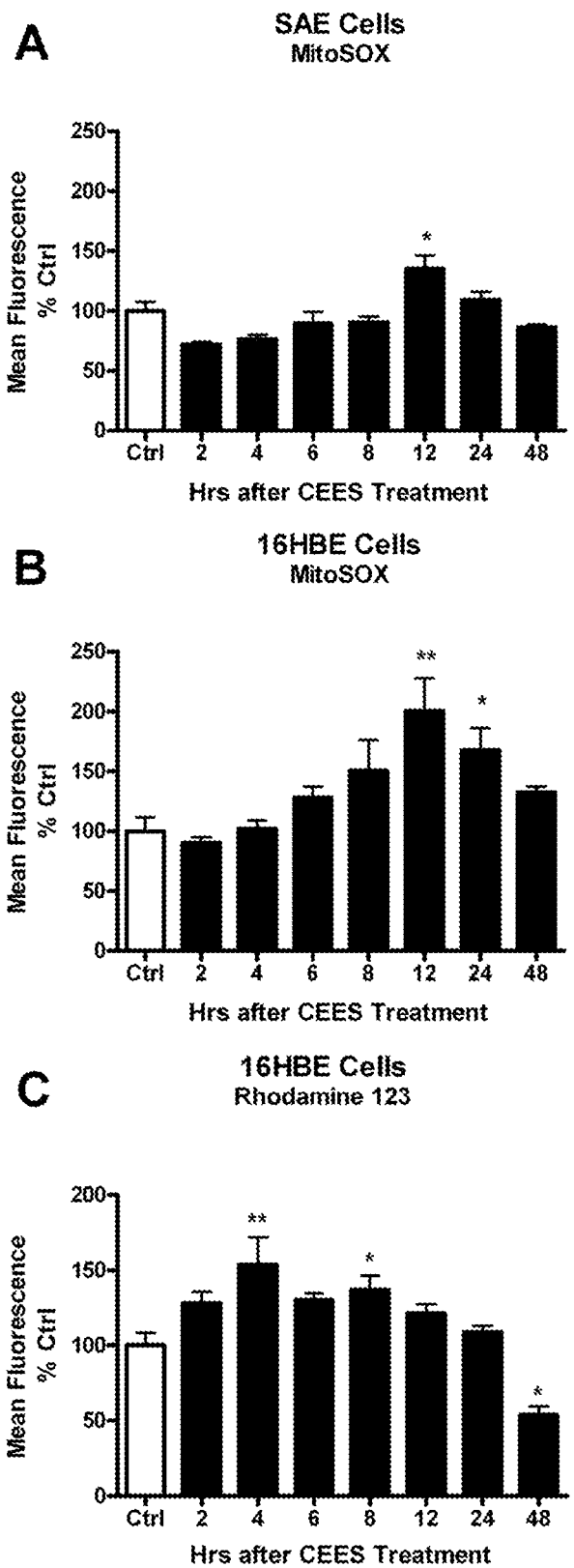
FIG. 3A-3C are graphs showing that CEES exposure produced increased levels of mitochondrial ROS dysfunction. SAE cells (Panel A) and 16HBE cells (Panel B) were treated with 900 μM CEES for 2, 4, 6, 8, 12, 24, and 48 h, after which cells were incubated with the mitochondrial ROS probe MitoSOX (Panel A and Panel B) for 1 h. (Panel C) 16 HBE cells were incubated with the mitochondrial membrane potential indicator Rhodamine 123 for 30 min. MitoSOX fluorescence correlated with increased ROS, where Rhodamine 123 fluorescence was inversely correlated with mitochondrial membrane potential.

Next CEES was examined to determine whether CEES exposure was associated with any mitochondrial dysfunction. Mitochondria need to maintain a membrane potential to actively make ATP. To examine this, measured Rho 123 fluorescence was measured, which is inversely correlated with mitochondrial membrane potential. Human lung 16HBE cells were exposed to CEES for 2, 4, 6, 8, 12, 24, and 48 h, after which the cells were incubated with Rho 123, and fluorescence was measured using flow cytometry. The results showed that CEES produced a decrease in mitochondrial membrane potential by 4 h, which persisted for 24 h as evidenced by the increase in Rho 123 fluorescence (FIG. 3C). Notably, there was a significant decrease in Rho 123 fluorescence at 48 h, which can be attributed to the cell death that would be expected to occur based on previous cell viability tests.

Specific Example 3

Metalloporphyrins Rescue Human Lung Cells from CEES-Induced Toxicity

Figure 4:
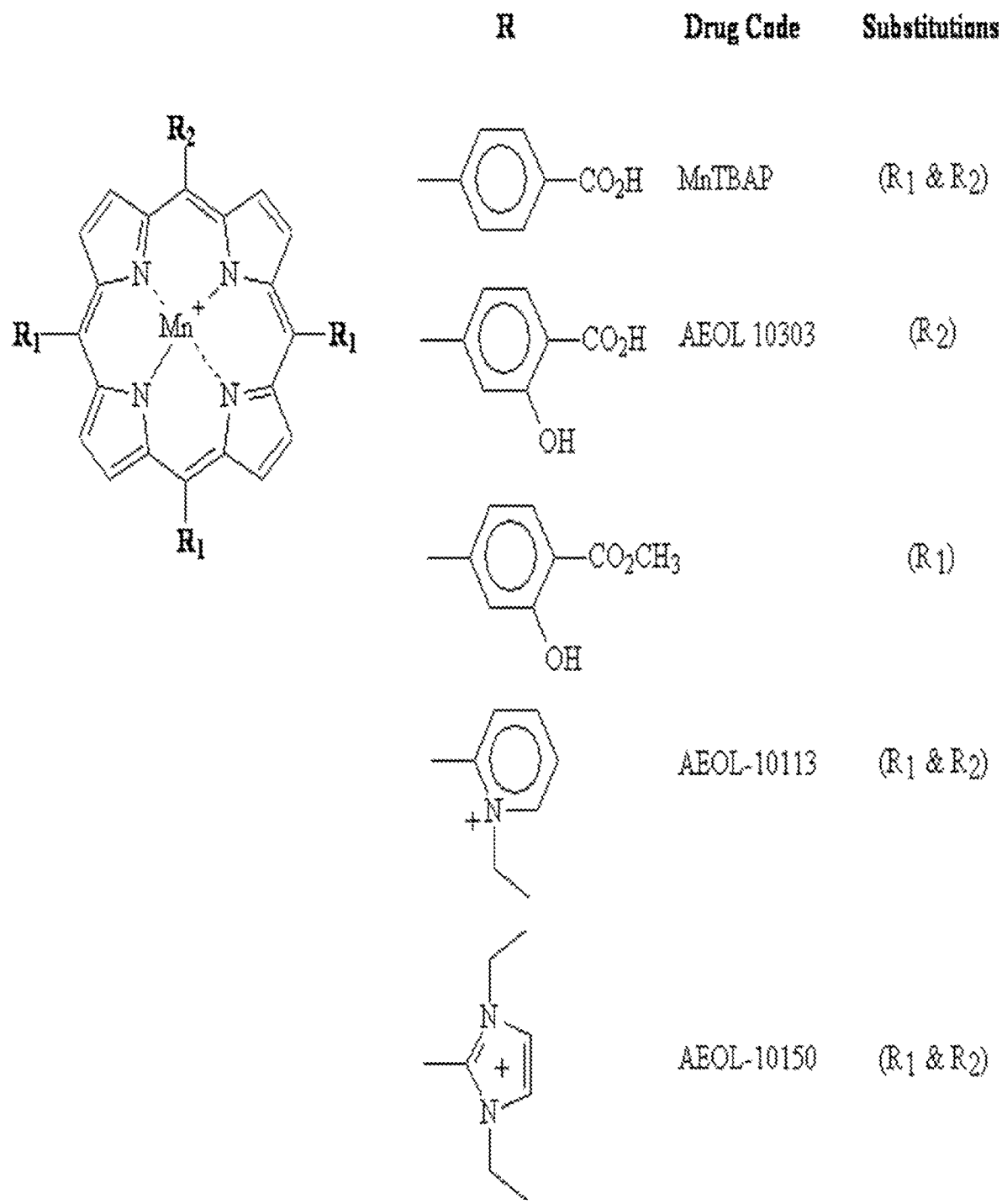
FIG. 4 shows chemical structures the catalytic antioxidant metalloporphyrins tested in specific examples 1-6, below.
Figure 5:
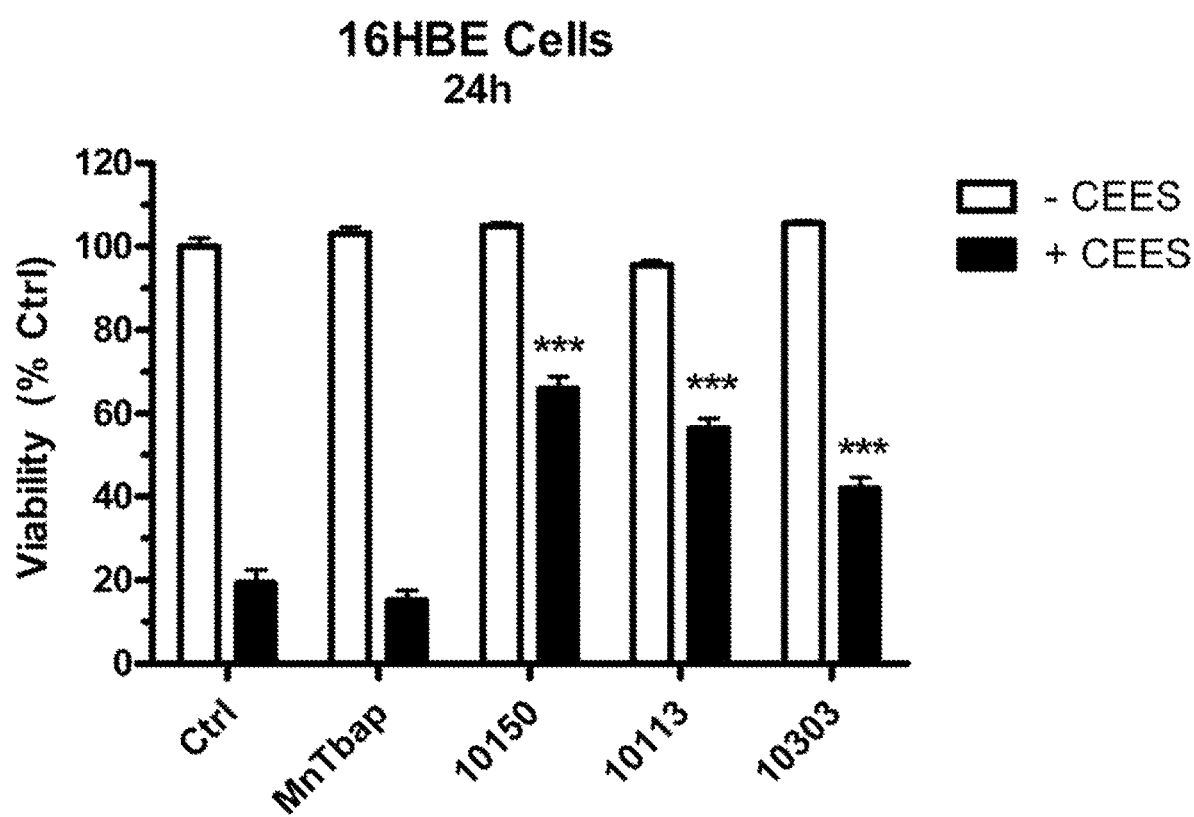
FIG. 5 is a graph showing the protective effects of metalloporphyrins on CEES-induced cell injury: 16HBE cells were grown to 90% confluence and exposed to 900 μM CEES for a total of 24 h. Cells were treated 1 h after the initial CEES exposure with AEOL 10150, AEOL 10113, AEOL 10303, or MnTBAP at a final concentration of 50 μM in the presence (black bars) or absence (white bars) of 900 μM CEES. Data represented as mean±S.E.M., n=4. ***, p<0.001 compared with CEES-only treatment group.

Several structurally different metalloporphyrins (AEOL 10150, AEOL 10113, AEOL 10303, and MnTBAP) were screened in 161-BE cells for efficacy against CEES toxicity 1 h after the initial exposure (FIG. 4). Cells were treated with CEES for 1 h at 37° C., after which the compounds of Formula 10150 (Formula VI, above), 10113 (Formula IX, above), 10103 (Formula VIII, above) and MnTBAP were added at a final concentration of 50 µM. After 24 h, cell viability was measured using calcein AM fluorescence. Three catalytic antioxidant compounds significantly increased cell viability in CEES-exposed cells to 60, 56, and 41% in the 10150, 10113, 10103 groups compared with only 20% in CEES-only exposed cells (FIG. 5). Of the four compounds tested, only MnTBAP did not show any protection.

Specific Example 4

AEOL 10150 Rescues Human Primary Airway Cells from CEES-Induced Toxicity

Figure 6:
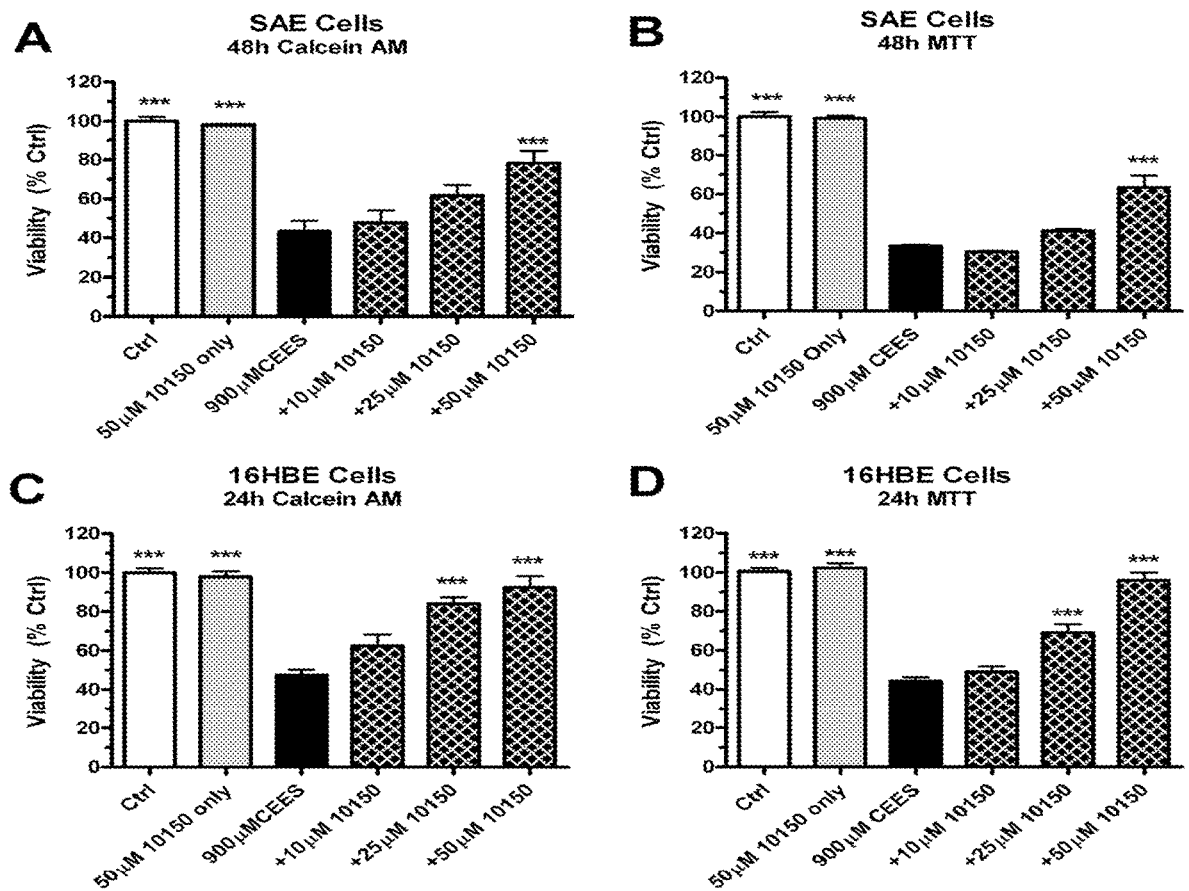
FIG. 6A-D are graphs showing the rescue effect of AEOL 10150 on CEES-induced cell death. SAE cells (Panel A and Panel B) and 16HBE cells (Panel C and Panel D) were exposed to 900 μM CEES with AEOL 10150 at 10, 25, and 50 μM concentrations added 1 h after CEES exposure. Cell viability was measured using both calcein AM (Panel A and Panel C) and MTT (Panel B and Panel D) staining with control values being defined as 100% viability. Data represented as mean±S.E.M., n=4. , p<0.01; * p<0.001 compared with CEES-only treated group.

Primary human lung SAE cells and 16HBE cells were exposed to 900 µM CEES for 48 h. Treatment with AEOL 10150 (10, 25, and 50 µM) occurred 1 h after the initial CEES exposure. AEOL 10150 (50 µM) alone did not change the viability of the cells, as measured by both the calcein AM (FIG. 6, A and C) and the MIT (FIG. 6, B and D) assays. CEES alone resulted in a 50% decrease in cell viability, and this was significantly attenuated at the highest concentration of AEOL 10150, to 80% of the control in SAE cells (FIG. 6, A and B) and nearly 90% in 16HBE cells (FIG. 6, C and D). Although neither 10 nor 25 µM AEOL 10150 showed a significant increase in viability in the SAE cells, 25 µM AEOL 10150 did show a significant increase in viability in the 16HBE cells. Similar results were obtained in both the calcein AM and the MTT assays used to assess cell viability.

Specific Example 5

AEOL 10150 Prevents CEES-Mediated Mitochondrial ROS and Dysfunction

AEOL 10150 were assessed to determine whether its cytoprotective effects are associated with CEES-mediated changes in mitochondrial ROS and dysfunction. Cells were grown to approximately 90% confluence and exposed to 900 µM CEES with and without AEOL 10150 (50 µM). Cells were incubated with MitoSOX 12 h after CEES exposure, and fluorescence was measured using flow cytometry. AEOL 10150 added 1 h after CEES treatments significantly decreased mitochondrial ROS compared with CEES exposed cells in both SAE (FIG. 7A) and 16HBE (FIG. 7B) cells. AEOL 10150 alone did not cause a change in mitochondrial ROS.

Figure 7:
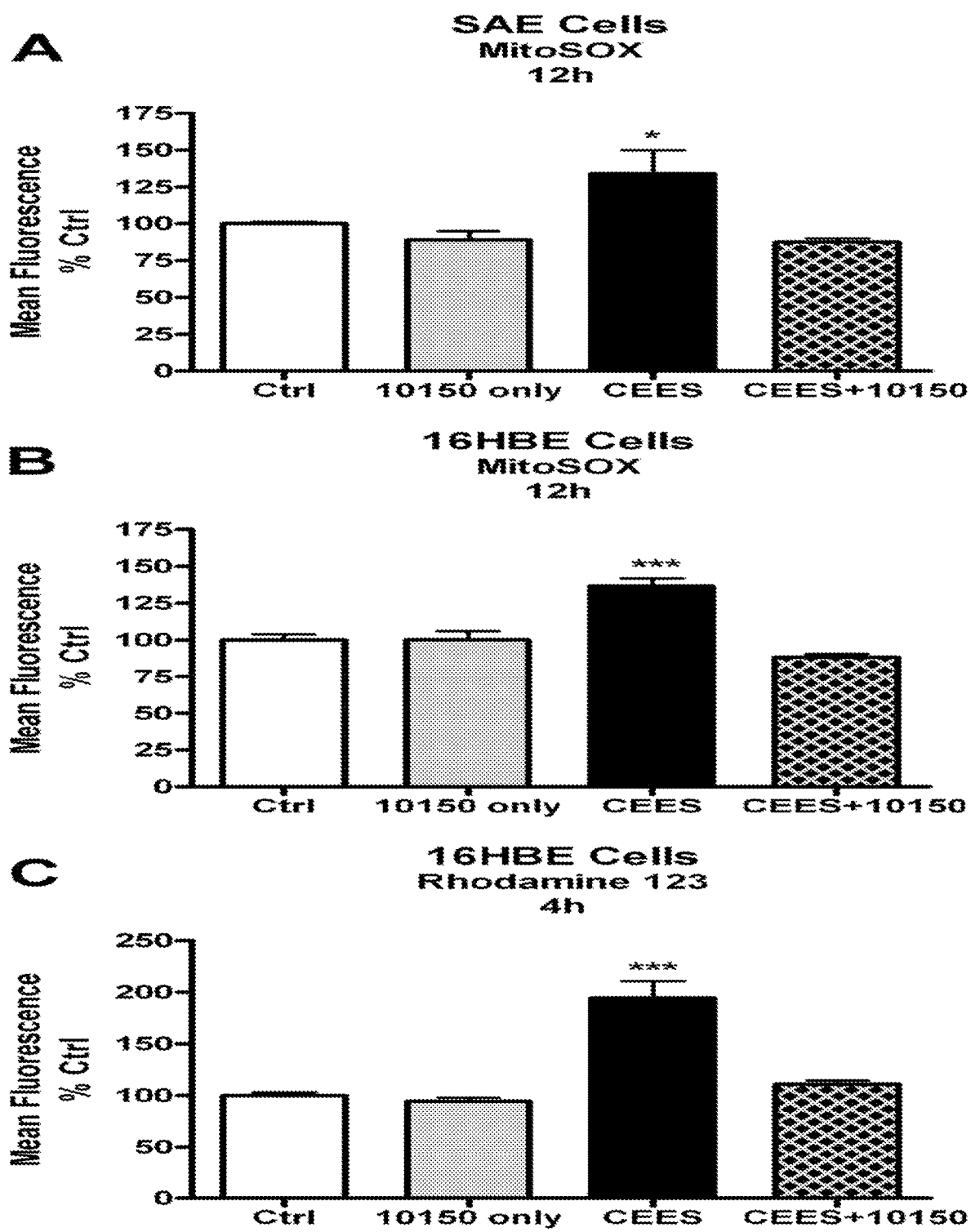
FIG. 7A-C are graphs showing that AEOL 10150 rescues CEES-induced increases in mitochondrial ROS and dysfunction. SAE cells (Panel A) and 16HBE cells (Panel B) were exposed to 900 μM CEES for 12 h. AEOL 10150 (50

Additionally, AEOL 10150 was assessed to determine if it can protect the mitochondria from CEES-induced dysfunction. Lung 16HBE cells were exposed to 900 µM CEES for 4 h with 50 µM AEOL 10150 added 1 h after the initial CEES exposure. The CEES-only treated groups showed an increase in Rhodamine 123 fluorescence, indicating a significant loss of mitochondrial membrane potential that was attenuated in the AEOL 10150-treated cells (FIG. 7C).

Specific Example 6

AEOL 10150 Prevents CEES-Induced Oxidative Stress

Oxidative stress can result from an imbalance between oxidant production and antioxidant defense. As discussed above, GSH is a major cellular antioxidant. So, the effect of CEES on total cellular GSH levels was determined as well as whether AEOL 10150 altered CEES-mediated changes in GSH levels. Human lung 16HBE cells were exposed for 12 h to CEES, and AEOL 10150 (50 µM) was added 1 h post-CEES treatment. AEOL 10150 alone did not alter intracellular GSH levels, whereas CEES caused a significant decrease in intracellular GSH levels (FIG. 8A AEOL 10150 treatment prevented the CEES-induced decrease in GSH, further implicating an imbalance in redox status of the cells caused by CEES that was reversible by AEOL'10150.

One consequence of oxidative stress is an increase in the oxidation of cellular macromolecules. A classic marker for DNA oxidation is the formation of 8-hydroxydeoxyguanosine (8O-HdG), which was determined 12 h after CEES exposure. CEES caused a significant increase in 80 HdG levels in lung 16HBE cells as measured by high-performance liquid chromatography (FIG. 8B). Moreover, AEOL 0.10150 added 1 h post-CEES exposure decreased CEES-mediated DNA oxidation. These data further support the role of oxidative stress in CEES-mediated injury that is ameliorated by the catalytic antioxidant metalloporphyrin, AEOL 10150.

Specific Example 7

AEOL 10150 Protects CEES-Induced Lung Injury in Rat

Figure 9:
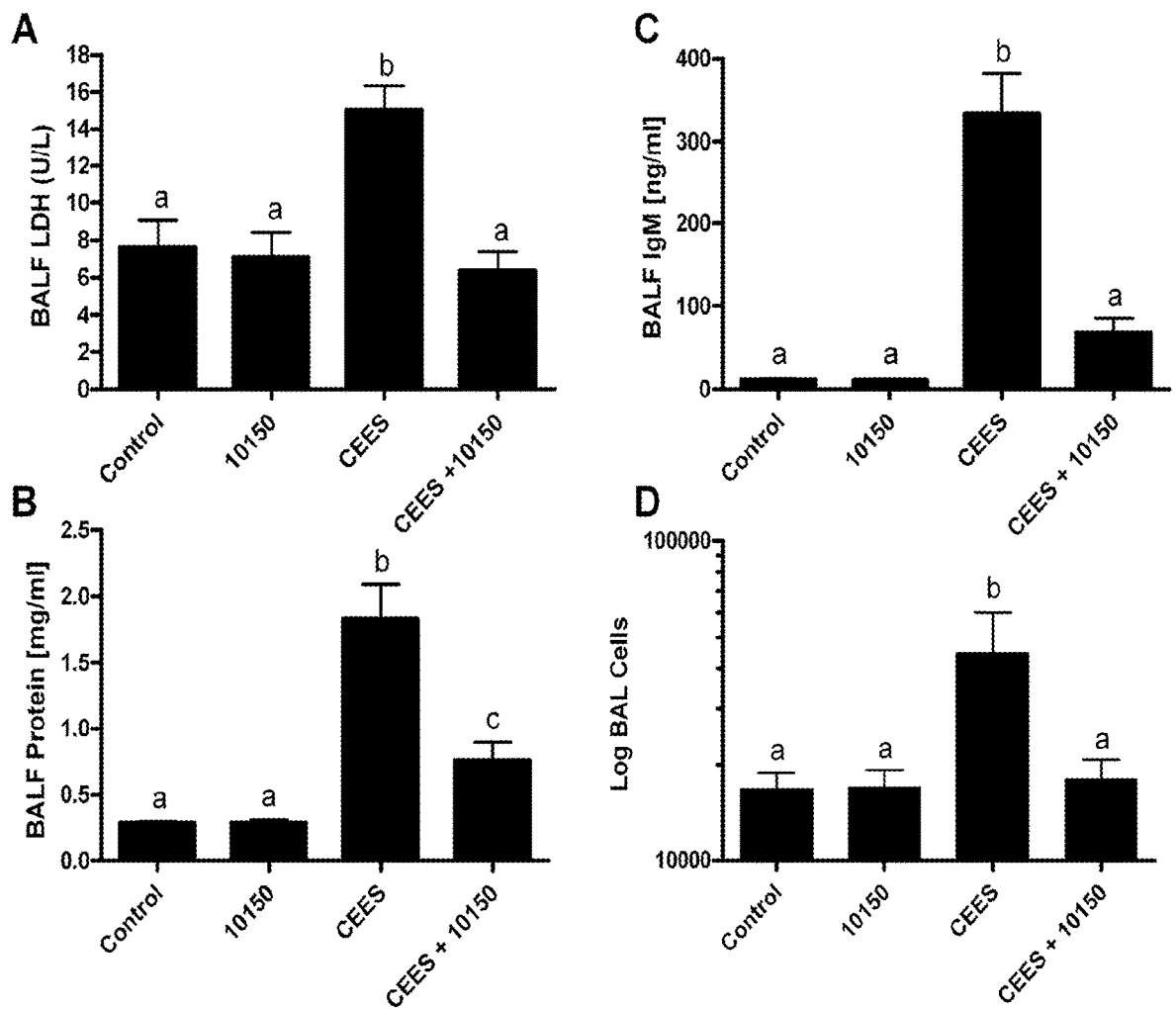

Rats were exposed to 5% CEES for 15 minutes and killed 18 hours later. Groups of rats received AEOL 10150 (5 mg/kg sc, bid) 1 hour after CEES exposure. Rat lungs were lavaged and markers of cytotoxicity, inflammation and edema were measured in bronchoalveolar lavage fluid (BALF). As shown in FIG. 9, CEES caused a significant increase in the ROS. Moreover, AEOL 10150 added 1 h post-CEES exposure decreased CEES-mediated DNA oxidation. These data further support the role of oxidative stress in CEES-mediated injury that is ameliorated by the catalytic antioxidant metalloporphyrin, AEOL 10150.

Specific Example 8

AEOL 10150 Reduces CEES-induced Cytotoxicity as Measured by LDH Release

CEES-induced cytotoxicity may be assessed by measuring LDH release in the lung. LDH release in the bronchoalveolar lavage fluid (BAL) is a marker of cellular injury in the epithelium. FIG. 10 shows levels of LDH release were not different between EtOH+PBS and EtOH+AEOL 10150 treated animals. Following CEES exposure with PBS treatment, LDH release doubled as compared to the control groups ($p<0.01$). When rats were administered AEOL 10150 following CEES-exposure, LDH levels were significantly attenuated as compared to the CEES+PBS group ($p<0.001$).

Specific Example 9

AEOL 10150 Reduces CEES-induced BAL Increases in Protein and IgM

Administering AEOL 10150 reduces alkylating agent-induced increases in protein and IgM in the lung. BAL in normal rats consists of macrophages and low levels of large proteins such as albumin. Measuring protein levels in the BAL is one way to measure the accumulation of extravascular protein in the airways. As shown in FIG. 11A, compared to EtOH+PBS or EtOH+AEOL 10150, protein levels in BAL were significantly increased as a result of 5% CEES+PBS ($p<0.001$). Protein levels in the BAL were significantly decreased from CEES+PBS when animals were administered AEOL 10150 ($p<0.001$). Although increased protein levels in BAL may not be a clear indicator of vascular permeability because it may also indicate lysis of damaged epithelium resulting from CEES exposure, the presence of very high molecular weight molecules such as IgM (900 kD) are clearly indicative of increased vascular permeability. Accordingly, FIG. 11B demonstrates that IgM levels in the BAL were significantly increased a result in CEES+PBS rats as compared to EtOH+PBS or EtOH+ AEOL 10150 ($p<0.001$). IgM levels were significantly decreased with CEES+AEOL 10150 treatment as compared to CEES+PBS. Combined, these data demonstrate that administration of the AEOL 10150 following CEES exposure decreased protein levels in BAL as well as IgM levels.

Specific Example 10

AEOL 10150 Treatment Reduces Levels of RBCs and Inflammatory Cells in BAL

Administering AEOL 10150 following alkylating agent exposure reduces levels of red blood cells (RBCs) and inflammatory cells in the lung. RBCs should not be present in the lung in any considerable levels unless there is hemorrhagic injury. Exposure to 5% CEES+PBS results in significantly increased hemorrhage as shown by increased RBC levels in the BAL ($p<0.001$). This CEES-induced damage is ameliorated with AEOL 10150 treatment 18 hours after CEES exposure ($p<0.05$). Levels of PMN or neutrophils in the BAL were significantly increased in the CEES+ PBS rats as compared to EtOH+PBS or EtOH+10150 ($p<0.001$). CEES-induced neutrophil increases were significantly decreased with AEOL 10150 treatment ($p<0.05$). While there was a decrease in macrophage levels with CEES exposure, this change did not reach significance as compared to the EtOH exposed animals.

Specific Example 11

Myeloperoxidase (MPO) in Lung Homogenate

MPO is a glycoprotein expressed in all cells of the myeloid lineage but is most abundant in the azurophilic granules of PMNs. Released MPO by activated PMNs measured in whole lung homogenate demonstrates tissue accumulation and is a useful complement to measurement of PMN in the BAL. MPO levels were significantly increased as a result of CEES+PBS indicating an increase in PMN tissue accumulation ($p<0.01$, FIG. 12). AEOL 10150 treatment after CEES treatment significantly decreased tissue accumulation of PMN ($p<0.05$).

Specific Example 12

AEOL 10150 Prevents CEES-induced Oxidative Stress

Oxidative stress occurs when oxidant production exceeds antioxidant defense. One marker of oxidative damage is DNA oxidation, which can be measured by the formation of 8-hydroxy-2-deoxyguanosine (8O HdG). 8O HdG significantly increased in CEES+PBS rats as compared to levels in EtOH+PBS ($p<0.01$) or EtOH+10150 ($p<0.05$) treatment 18 hours after exposure as measured by HPLC (FIG. 13). When rats were exposed to CEES and then received AEOL 10150, 8O-HdG levels were significantly decreased as compared to CEES+PBS ($p<0.05$). These data further support the role of oxidative stress in CEES-mediated injury that is ameliorated by the catalytic antioxidant metalloporphyrin, AEOL 10150.

Another marker of oxidative damage is the formation of lipid peroxidation products including 4-hydroxynonenal (4-HNE). 4-HNE is a major product of total unsaturated aldehydes formed during lipid peroxidation. Measurement of 4-FINE levels in the lung 18 hours after CEES exposure resulted in a significant increase compared with EtOH+PBS treated rats (FIG. 14). AEOL 10150 significantly inhibited CEES-induced lipid peroxidation.

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in cellular and molecular biology, chemistry, or in the relevant fields are intended to be within the scope of the appended claims.

The disclosures of all references and publications cited above are expressly incorporated by reference in their entireties to the same extent as if each were incorporated by reference individually.

What is claimed is:

1. A method of treating an injury associated with exposure to an alkylating agent in a subject, wherein the alkylating agent is chlorine gas, said method comprising the step of:
   administering to a subject in need thereof an effective amount of a compound of formula

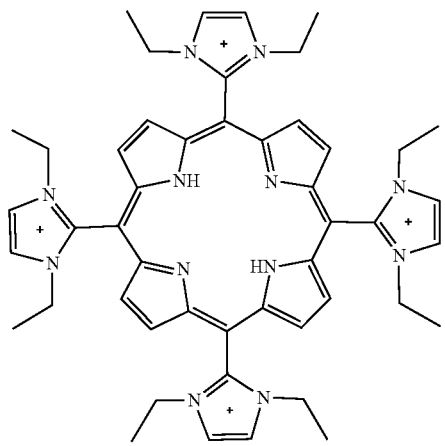

or a pharmaceutically acceptable salt thereof, wherein the exposure is through inhalation exposure or topical exposure, and said injury is damage to the skin, eyes or respiratory tract of said subject.

2. The method of claim 1, wherein the compound is bound to a metal.

3. The method of claim 2, wherein the metal is selected from the group consisting of manganese, iron, cobalt, copper, nickel, and zinc.
4. The method of claim 3, wherein the compound is bound to manganese.
5. The method of claim 4, wherein the compound is:
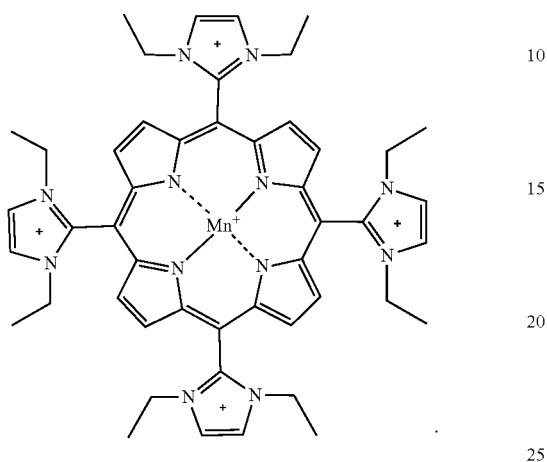
\* \* \* \* \*